United States Patent
Wiklund et al.

(10) Patent No.: US 9,383,237 B2
(45) Date of Patent: Jul. 5, 2016

(54) FLUID VISUALISATION AND CHARACTERISATION SYSTEM AND METHOD; A TRANSDUCER

(71) Applicants: SIK—THE SWEDISH INSTITUTE FOR FOOD AND BIOTECHNOLOGY, Gothenburg (SE); CAPE PENINSULA UNIVERSITY OF TECHNOLOGY, Cape Town (ZA)

(72) Inventors: Johan Wiklund, Landvetter (SE); Rainer Haldenwang, Durbanville (ZA); Reinhardt Kotze, Cape Town (ZA)

(73) Assignees: CAPE PENINSULA UNIVERSITY OF TECHNOLOGY, Cape Town (ZA); SP TECHNICAL RESEARCH INSTITUTE OF SWEDEN, Boras (SE)

( * ) Notice: Subject to any disclaimer, the term of this patent is extended or adjusted under 35 U.S.C. 154(b) by 0 days.

(21) Appl. No.: 13/929,186

(22) Filed: Jun. 27, 2013

(65) Prior Publication Data

US 2013/0345994 A1    Dec. 26, 2013

Related U.S. Application Data

(63) Continuation of application No. PCT/IB2012/053244, filed on Jun. 27, 2012.

(30) Foreign Application Priority Data

Aug. 4, 2011   (ZA) .................................... 11/05745

(51) Int. Cl.
*G01F 1/05* (2006.01)
*G01F 1/20* (2006.01)
(Continued)

(52) U.S. Cl.
CPC .. *G01F 1/66* (2013.01); *G01F 1/34* (2013.01); *G01F 1/662* (2013.01); *G01F 1/663* (2013.01);
(Continued)

(58) Field of Classification Search
CPC ......................................................... H04L 1/00
USPC ............. 702/19, 46, 48, 50, 54, 56, 185, 187, 702/188, 190; 73/1.82, 597; 181/106
See application file for complete search history.

(56) References Cited

U.S. PATENT DOCUMENTS 5,488,952 A * 2/1996 Schoolman ................... 600/443
5,777,892 A * 7/1998 Nabity et al. ................. 702/143
(Continued)

FOREIGN PATENT DOCUMENTS

WO    0169231 A1   9/2001
WO    2009037435 A2   3/2009

OTHER PUBLICATIONS

Donald W. Baker, "Pulsed Ultrasonic Doppler Blood-Flow Sensing," IEEE Transactions on Sonics and Ultrasonics, vol. SU-17, No. 3, Jul. 1970, pp. 170-185.
(Continued)

*Primary Examiner* — Gregory J Toatley
*Assistant Examiner* — Felix Suarez
(74) *Attorney, Agent, or Firm* — Cantor Colburn LLP

(57) ABSTRACT

A fluid visualization and characterization system includes a measuring section with a housing defining a fluid flow path for fluid flow. The measuring section includes one or more transducers to emit ultrasonic signals into the fluid flow, and at least one receiver to receive reflections of the ultrasonic signal from reflectors in the fluid flow. The system includes a memory for storing data and a processor operatively connected to the memory. The processor comprises several modules. A velocity estimating module is configured to apply one or more velocity estimation algorithms to received reflections of the ultrasonic signal, or data indicative thereof, to determine a velocity profile of the fluid flow. A deconvolution module is configured to apply a deconvolution algorithm at least to the determined velocity profile to determine a true velocity profile of the fluid flow. A fluid visualization and characterization module is configured to determine characteristics of the fluid and/or fluid flow in by using the determined velocity profile and/or the true velocity profile.

24 Claims, 14 Drawing Sheets

(51) Int. Cl.
*G01F 1/22* (2006.01)
*G01F 1/32* (2006.01)
*G01F 1/66* (2006.01)
*G01F 1/34* (2006.01)
*G01F 1/704* (2006.01)
*G01F 15/00* (2006.01)
*G01F 15/02* (2006.01)
*G01N 11/08* (2006.01)

(52) U.S. Cl.
CPC .............. *G01F 1/668* (2013.01); *G01F 1/704* (2013.01); *G01F 15/00* (2013.01); *G01F 15/024* (2013.01); *G01N 11/08* (2013.01)

(56) References Cited

U.S. PATENT DOCUMENTS

| | | | | |
|---|---|---|---|---|
| 5,987,385 | A | * | 11/1999 | Varsamis et al. ................ 702/6 |
| 6,199,423 | B1 | * | 3/2001 | Logue et al. .................... 73/1.82 |
| 7,614,302 | B2 | * | 11/2009 | DiFoggio et al. ............... 73/597 |
| 7,823,689 | B2 | * | 11/2010 | Aronstam et al. ............. 181/106 |
| 7,826,973 | B2 | * | 11/2010 | Washbourne et al. ............ 702/6 |
| 2008/0163700 | A1 | * | 7/2008 | Huang ........................ 73/861.25 |
| 2011/0289675 | A1 | * | 12/2011 | Dunki-Jacobs et al. ........... 4/668 |

OTHER PUBLICATIONS

William D. Barber et al., "A New Time Domain Technique for Velocity Measurements Using Doppler Ultrasound," IEEE Transactions on Biomedical Engineering, vol. BME-32, No. 3, Mar. 1985, pp. 213-229.

R.A. Black et al., "Pulsed Doppler ultrasound system for the measurement of velocity distributions and flow disturbances in arterial prostheses," Journal of Biomedical Engineering, vol. 11, No. 1, Jan. 1, 1989, pp. 35-42.

Patrice Flaud et al., "Deconvolution Process in Measurement of Arterial Velocity Profiles Via an Ultrasonic Pulsed Doppler Velocimeter for Evaluation of the Wall Shear Rate," Ultrasound in Medicine & Biology, vol. 23, No. 3, Jan. 1, 1997, pp. 425-436.

P.E. Hughes et al., "Pulsatile Velocity Distribution and Wall Shear Rate Measurement Using Pulsed Doppler Ultrasound," J. Biomechanics, vol. 27, No. 1, Jan. 1, 1994, pp. 103-110.

Jens E. Jorgensen et al., "Physical characteristics and mathematical modelling of the pulsed ultrasonic flowmeter," Medical and Biological Engineering, vol. 11, No. 4, Jul. 1973, pp. 404-421.

J.E. Jorgensen et al., "An Analytical Procedure of Calibration for the Pulsed Ultrasonic Doppler Flow Meter," Transactions of the ASME, Journal of Fluids Engineering, vol. 96, No. 2, Jun. 1974, pp. 158-167.

* cited by examiner

FLUID VISUALISATION AND CHARACTERISATION SYSTEM AND METHOD; A TRANSDUCER

CROSS-REFERENCE TO RELATED APPLICATIONS

This application is a by-pass continuation application of International Application No. PCT/IB2012/053244, which has an international filing date of 27 Jun. 2012, and which claims priority to South African Patent Application No. 2011/05745, filed 4 Aug. 2011.

BACKGROUND OF THE INVENTION

1. Field of the Invention

This invention relates to a method and system for visualizing and characterising fluids flowing in a means defining a fluid flow path.

2. Related Art

Pulsed Ultrasound Velocimetry (PUV) is a technique for measuring an instantaneous velocity profile in liquid flow along a pulsed ultrasonic beam axis. The instantaneous velocity profile is obtained by detecting the relative time lags of backscattered ultrasound echoes from moving particles between successive pulse emissions. As shown in the article by D. W. Baker, 'Pulsed Ultrasonic Doppler Blood-Flow Sensing', IEEE Transactions on Sonics and Ultrasonics, vol. SU-17, No. 3, July 1970, hereby incorporated by reference, ultrasonic signals may be used for non-invasive measurements of fluid velocities.

It would be desirable to adapt such techniques to provide a method for fluid flow metering, visualization and rheological characterisation.

Commercially available ultrasonic flow meters are based on either transit-time or pulsed Doppler methods. It would be desirable to use a combination of transit-time and pulsed ultrasound methods to improve volumetric flow rate measurements and thereby also improve the accuracy of in-line rheometry.

Methods for in-line rheometry are often based on traditional tube viscometry concepts where shear rates are obtained from measurements of the volumetric flow rate in the pipes, and the shear stresses at inner pipe walls are determined from simultaneous measurements of pressure difference over fixed distances along the pipe.

The UVP technique with Pressure Difference (PD) measurements, usually referred to as the UVP+PD methodology, is used to characterise fluids flowing in fluid flow paths, e.g., in pipes.

The UVP+PD methodology has been applied to a wide range of fluid systems, including a range of model and industrial fluids and suspensions, containing both soft and hard particles and fibres with diameters from a few nanometers up to several centimeters in length. It has also been evaluated for several potential industrial applications, such as polymer melt rheology, paper pulp, concentrated mineral suspensions, and fat crystallisation.

However, no commercial UVP+PD system is readily available on the market and systems used until now have been typically based on off-the-shelf transducers and electronics and are therefore more suited for simple flow characterisation with limited accuracy without meeting industrial requirements.

Also, conventional UVP+PD instruments typically used in research environments, systems/instrumentation and methodologies do not possess robustness and accuracy required in industrial applications. One problem is that conventional off-the-shelf type transducers and instrumentation used in UVP (and UVP+PD) systems are not designed for measurements inside small and complex geometries, such as industrial processing pipes. Also, conventional UVP instruments have been adapted from simplified designs and methodologies found in the medical industry for measurement of blood flow. However, human blood, and also water, is not attenuating compared to current industrial fluid systems and thus the existing UVP instruments are not able to provide desired functionality to the latter.

It is therefore an object of the present invention to at least address the above-mentioned problems and issues.

SUMMARY OF THE INVENTION

According to a first aspect of the invention, a method is provided for visualizing and characterising fluids flowing in a means defining a fluid flow path, the method comprising:
  emitting a high frequency (ultrasonic) acoustic signal into a fluid flow in a means defining a fluid flow path by way of a first transducer, the first transducer comprising a delay line material;
  receiving at least reflection/s of the ultrasonic signal emitted by the at least one delay line transducer from reflector/s in the fluid flow path;
  applying one or more algorithms to the received reflection/s of the ultrasonic signal, or data indicative thereof, to determine a velocity profile of fluid flow as well as information relating to the nature/quality of individual gated sampling regions in the means defining the fluid flow path;
  applying a deconvolution algorithm to the determined velocity profile to determine a deconvolved velocity profile of the fluid flow in the means defining the fluid flow path; and
  determining fluid flow characteristics of the fluid flowing in the means defining the fluid flow path by using the determined velocity profiles and/or the deconvolved velocity profile.

The method may comprise determining fluid and fluid flow characteristics by way of a fitting procedure, for example, or a non-model approach.

The first transducer may be a delay line transducer. The method may comprise receiving the reflection/s of the high frequency signal by way of a second delay line transducer in line with the first delay line transducer. Both transducers are able to operate in transmitting and receiving mode, i.e. each transducer is able to measure velocity profiles independently. Transducers are mounted at opposite sides so that when one transmits a signal the other receives (or vice-versa) in order to record a time-of-flight measurement used for calculation of the velocity of sound in the fluid medium.

The method may comprise emitting a series of high frequency acoustic signals into the fluid flowing in the means and receiving associated reflections. The high frequency signals emitted may be acoustic signals in the ultrasound frequency range.

The method may comprise simultaneously applying a plurality of velocity determining algorithms to determine the velocity profile. The velocity determining algorithms may be time domain and frequency domain algorithms which are applied at substantially the same time for enhanced accuracy and quality of measured velocity profiles (spectral information and velocity estimation).

The means defining the fluid flow path may comprise a pipe in fluid communication with a fluid circuit or network.

Applying the deconvolution algorithm may comprise the steps of:
- receiving and storing the velocity profile, measured velocity of sound parameter, and a measured waveform shape;
- determining a normalised sample window from the measured waveform shape by detecting an envelope of the measured waveform shape and dividing all sample points on the sample window by the sample window's maximum magnitude value;
- determining a length of sample window by multiplying a time axis with the measured velocity of sound parameter;
- re-sampling both recorded velocity profile and determined sample window so that the number of samples correspond to correct distances of the sample window and radial distance of the stored velocity profile;
- multiplying the stored velocity profile by an integral of a sample window within the flow field to obtain a first multiplication product;
- applying a Fast Fourier Transform (FFT) algorithm to the first multiplication product to obtain a first FFT result;
- applying a FFT algorithm to the sample window to obtain a second FFT result;
- dividing the first FFT result by the second FFT result to obtain a first division quotient;
- applying a low pass filter in the frequency domain to the first division quotient to obtain a low pass filtered first division quotient; and
- applying an inverse FFT to the low pass filtered first division quotient to obtain the deconvolved velocity profile.

The method may comprise applying a smoothing filter to the deconvolved velocity profile (such as moving average filters) if necessary. The method may comprise applying time-gain compensation algorithms and wall-filters to received reflections of the high frequency signals, e.g., low-pass (and high-pass filters) such as Chebyshev type II filters or the like.

The velocity of sound may be determined using only a single transducer.

The sample window's maximum magnitude value may be the peak of envelope.

The sample window may be provided in terms of normalised voltage vs. time.

The sample window may need to be described by at least 10 sample points for accurate deconvolution.

For the step of re-sampling, it will be appreciated that if the velocity profile is measured across a radial distance of 20 mm and the profile consists of 100 sample points, and the sample window length=5 mm, then the sample window should consist of 25 sample points.

The method may comprise operating the first transducer such that a focal point of the ultrasound signal or beam is situated at a surface of the delay line material, thus ensuring that no velocity measurements are made within the transducer's near-field distance, where the pressure field is highly irregular. The design also ensures that maximum amplitude and narrowest diameter of the beam is situated at a surface of the delay line material thereby, enabling accurate measurements directly from the transducer surface.

The method may comprise emitting a plurality of ultrasound signals and receiving associated reflections thereof from reflectors by way of reflection of the high frequency signal from a plurality of delay line transducer pairs.

The method may comprise emitting a plurality of acoustic signals and receiving associated reflections over pre-defined time windows corresponding to a large number of sampling regions in the fluid.

The method may comprise measuring a pressure difference over a fixed distance in the means defining the fluid flow. The shear stress distribution may be determined substantially simultaneously from a measurement of the pressure difference. This occurs substantially simultaneously with the velocity profile determination, deconvolved velocity profile, or both. It will be appreciated that the method may comprise using the pressure difference measurement in combination with the deconvolved velocity profile to determine shear viscosities and rheological parameters.

The determined velocity profile may be an instantaneous radial velocity profile. The method may comprise continuously determining velocity profiles of fluid flow in the pipe in real-time both in a direction of fluid flow and against the direction of the fluid flow by way of the two direct-line transducers installed at opposite sides of one another in the pipe.

The method may comprise applying smoothing filters to received reflections of the high frequency signals, e.g., singular value decomposition, finite impulse response, infinite impulse response, moving averages filters, or the like. The method may comprise applying smoothing filters to the determined velocity profiles and/or deconvolved velocity profiles, e.g. a Savitzky-Golay or Moving Average smoothing filter.

The method may comprise integrating determined velocity profiles and/or deconvolved velocity profiles to determine volumetric flow rates of fluids in the pipe. Instead, or in addition, the method may use transit times, e.g., time of flight measurements to determine the volumetric flow rates.

The method may comprise determining acoustic properties, such as, attenuation of ultrasound and sound velocity are continuously directly in-line, substantially in real-time.

The method may comprise determining concentration of solids (e.g. Solid Fat Content, SFC) in a pipe directly in-line by using velocity of sound and attenuation measurements.

The method may comprise the steps of matching a theoretical velocity profile vs. radial position onto experimental data i.e. the point velocities vs. radial position obtained from the Doppler shifts associated with their sampling regions and the corresponding pressure drop over a fixed distance) and identifying one or more rheological properties of the fluid flow from a mathematical relationship curve that matches best. It will be noted that the recorded velocity profile and pressure drop measurement is 'matched' with available rheological models stored in a database. Also, it will be noted that the velocity vs. position curve is typically the determined velocity.

The characteristics of the fluid flowing in the pipe may comprise rheological properties and/or parameters including fluid consistency index, flow behaviour index, yield stress, or the like.

The method may comprise calculating the shear rate and stress at each of a plurality of positions in the fluid flow.

The method may comprise determining shear viscosities and rheological model parameters from a non-linear fitting procedure of determined velocity profiles and measured pressure differences to rheological models. Alternatively, the method may comprise using a non-model approach, to determine shear rate distribution from a velocity gradient of the determined velocity profiles and optionally a shear stress at a wall of the pipe, e.g., via cubic-spline interpolation or polynomial model-fitting followed by numerical derivation. In this way, the present invention advantageously ameliorates the existing problems with inaccurate shear rate distributions caused by the inherent fluctuations of the mathematical fitting methods used (e.g. cubic-spline or polynomial).

It will be appreciated that the method may comprise applying a smoothing filter, e.g., a Savitzky-Golay smoothing filter to the determined velocity profiles and/or deconvolved velocity profiles prior to obtaining the velocity gradient (shear rate distribution).

According to a second aspect of the invention, there is provided a fluid visualization and characterisation system comprising:
 a measuring section comprising housing which comprises
  a means defining a fluid flow path for fluid flow, the measuring section comprising at least:
   a first transducer, which may comprise a delay line material, configured to generate and emit a high frequency signal into the fluid flow in the means defining the fluid flow path; and
   a receiver configured at least to receive reflection/s of the high frequency signal emitted by the at least one delay line transducer from reflector/s in the fluid flow;
 a memory for storing data; and
 a processor operatively connected to the memory, the processor comprising:
  a velocity estimating module configured to apply one or more velocity estimation algorithms (time and frequency domain) to the received reflection/s of the high frequency signal, or data indicative thereof, to determine a velocity profile of fluid flow in the means defining the fluid flow path;
  a deconvolution module configured to apply a deconvolution algorithm to the determined velocity profile to determine a true velocity profile of the fluid flow in the means defining the fluid flow path; and
  a fluid characterisation module configured at least to determine characteristics of the fluid flow in the means defining the fluid flow path by using the determined velocity profile and/or the true velocity profile.

The means defining the fluid flow path may comprise a pipe in fluid communication with a fluid circuit or network.

The receiver may be a second transducer in line with or adjacent to the first transducer. The system may comprise a plurality of delay line transducer pairs. In certain example embodiments, the first transducer may also comprise the receiver if necessary or expedient to do so.

The measuring section is configured to house a housing for differential pressure and temperature sensor(s). The means may comprise a unit that should be installed as a section in the pipe loop or fluid network or circuit. In other example embodiments, the measuring system, particularly the measuring section, is attachable to a pipe in a pipe or fluid network.

The system may comprise a signal generator configured to generate a series of high frequency signals or pulses for emission by the first delay line transducer. The high frequency signals emitted may be acoustic signals in the ultrasound frequency range. The signal generator may be configured to generate pulsed acoustic signals for emission by the first delay line transducer.

The processor or system may comprise one or more amplifiers to amplify both transmitted and received signal, waveforms, or pulses, for example, using a time-gain compensation. In particular, the processor may be configured to apply time-gain compensation algorithms and wall-filters to received reflections of the high frequency signals, e.g., low-pass (and high-pass filters) such as Chebyshev type II filters or the like.

The velocity estimating module may be configured to apply simultaneously a plurality of velocity determining algorithms to determine the velocity profile. The velocity determining algorithms may be time domain and frequency domain algorithms which are applied at substantially at same time for enhanced accuracy and quality of measured velocity profiles (spectral information and velocity estimation).

The deconvolution module may be configured to:
 receive the velocity profile, velocity of sound parameter, and a waveform shape;
 determine a normalised sample window from the measured waveform shape by detecting an envelope of the measured waveform shape and dividing all sample points on the sample window by the sample window's maximum magnitude value;
 determine a length of sample window by multiplying a time axis with the measured velocity of sound parameter;
 re-sample both recorded velocity profile and determined sample window so that the number of samples correspond to correct distances of the sample window and radial distance of the stored velocity profile;
 multiply the stored velocity profile by an integral of a sample window within the flow field to obtain a first multiplication product;
 apply a Fast Fourier Transform (FFT) algorithm to the first multiplication product to obtain a first FFT result;
 apply an FFT algorithm to the sample window/sample volume to obtain a second FFT result;
 divide the first FFT result by the second FFT result to obtain a first division quotient;
 apply a low pass filter to the first division quotient to obtain a low pass filtered first division quotient;
 apply an inverse FFT to the low pass filtered first division quotient to obtain the deconvolved velocity profile; and
 apply a smoothing filter to the deconvolved profile in order to remove unwanted noise and enhance quality of the data.

The sample window may need to be described by typically at least 10 sample points for accurate deconvolution.

The first transducer may be configured such that a focal point of the ultrasound signal or beam is situated at a liquid-wall interface, thus ensuring that no velocity measurements are made within the transducer's near-field distance, where the pressure field is highly irregular.

It will be appreciated that the transducer may comprise any kind of acoustic transducer that can be used for pulsed ultrasound velocimetry, and which is preferably fitted with a "delay line" at each transducer front. The delay line may be fixed to the transducer front.

The delay line may comprise a material designed for beam forming and contains the near field distance in which the acoustic pressure is non-uniform and goes through a series of maxima-minima. (Beam forming)

The delay line may also provide an optimal acoustic beam path and coupling between the transducer and the fluid under investigation.

The shape/dimensions and material characteristics of the delay line may be optimised to reduce parasitic echoes and blind spots within the focal zone of the transducers and produce a narrow beam with an extended focal zone for increased acoustic penetration depth from the transducer front. (Beam focusing)

The length of the delay line may be linked to a quarter wave length at the operating frequency of the transducer so that the focal point with maximum acoustic pressure is located at a liquid/wall interface in use. (acoustic coupling/matching, maximum energy transfer)

It should be noted that the terms "delay line", "acoustic wedge", "acoustic couplant", etc. are sometimes used for a special type of transducer or transducer accessory designed for non-destructive testing. However, in the case of the present example embodiment the replaceable "delay line" material is used to delay the emitted ultrasound signal so that it can be used to obtain optimum acoustic beam properties, such as beam forming, beam focusing, acoustic coupling, impedance matching, optimum beam path and sensor protection.

An "acoustic wedge" on the other hand is designed, for example, to generate or eliminate different types of wave (e.g. shear/longitudinal waves) in any solid or semi-solid materials that could be used for non-invasive measurements. An "acoustic couplant" is defined as a material used to ensure maximum energy transfer between the ultrasonic transducer and the material. In the present invention it is preferred to use a non-invasive sensor setup for pulsed ultrasound measurements.

It should be noted that in this invention the term "delay line" material could mean "acoustic wedge", "acoustic couplant", or a combination thereof, that has multiple functionalities such as beam forming, beam focusing, acoustic coupling, impedance matching, desired beam path generation and/or elimination and sensor protection.

The system may comprise an absolute pressure sensor or a differential pressure sensor for obtaining a pressure difference between locations along a length of the pipe. The system may also comprise one or more temperature sensors.

The system may comprise means for passing a section of the received signal in an adjustable time window relative to the transmitted waveform (pulse), thereby providing a gated received signal that may be filtered, demodulated to produce a frequency shifted sample signal and to perform operations to determine the frequency shift, time- or phase delay associated with a region of the fluid flow.

The processor may be configured to adjust the time window to determine local velocity in each sampling volume and compute instantaneous velocity distribution as a function of time or distance along each measuring axis, line.

The processor may be configured to determine one or more shear-dependent viscosities and model parameters of the fluid flow and to calculate shear rate and shear stress distribution.

The processor may further be configured to determine one or more acoustic properties, such as, attenuation of ultrasound and the sound velocity directly in-line, in real-time. The information may be used to determine e.g. the total concentration of Solid Fat Content (SFC) directly in-line and particle size (frequency sweep).

The system may comprise a flow depth sensor configured to receive flow depth/height data of fluid flowing in an open channel or flume. The system may be configured to determine characteristics of fluid flowing in the flume or open channel by obtaining a single velocity profile combined with a flow height/depth measurement. (UVP+FD methodology)

The fluid characterisation module may be configured to determine shear rate distribution substantially simultaneously from a measurement of the pressure difference. In particular, the fluid characterisation module may be configured to use the pressure difference from pressure sensors in combination with the deconvolved velocity profile to determine shear viscosities and rheological model parameters.

The fluid characterisation module may be configured to determine shear viscosities and rheological model parameters by a non-linear model fitting procedure of determined velocity profiles and/or measured pressure differences to rheological models. Alternatively, the fluid characterisation module may be configured to use a non-model approach, known as the gradient method, to determine shear rate distribution from a velocity gradient of the determined velocity profiles and optionally a shear stress at a wall of the pipe, e.g., via cubic-spline interpolation or polynomial model-fitting followed by numerical derivation.

The measuring section of the housing may typically comprise two transducer ports for housing the first and second delay line transducers, substantially opposite each other and flush with the pipe wall. The delay line material of the transducers are flush with the inner surface diameter of the pipe, thus ensuring no flow distortion caused by cavities used in previous methodologies. The housing may also comprise pressure sensor ports for housing pressure sensors and one or more temperature sensor ports for housing one or more temperature sensors.

The housing may also comprise or be in flow communication with one or more pressure adaptors, typically upstream and downstream from the measuring section. Each pressure adaptor may comprise an inlet and outlet port interspaced by a flow chamber, the inlet and outlet ports not being in straight-line alignment with each other. The inlet and outlet ports may be in flow communication with the flow chamber, the inlet port being located upstream from the outlet port. The inlet port may be laterally spaced from the outlet port.

According to a third aspect of the invention, there is provided a transducer comprising:
  a housing;
  a transducer element for receiving and/or transmitting a ultrasound signal; and
  a delay line element operatively connected to the transducer element, the delay line element having one or more functionalities including one or more of beam forming, beam focusing, acoustic coupling, impedance matching, desired beam path generation and/or elimination and sensor protection.

The transducer element may be a piezo element.

The delay line material may be made of one or more of Polycarbonate (PC), Parylene, Epotek or Rexolan or other acoustically suitable material.

The acoustic properties of the delay line material may be chosen so that the acoustic impedance and the velocity of sound are as close as possible to that of water (or other industrial fluid) or solid/semi-solid materials such as steel, for example.

The delay line material may be glued or die cast directly to a front matching material or a piezo element of the transducer. Existing delay lines are usually just in contact with the front matching material using a gel or similar acoustic coupling material and only provide an acoustic coupling (impedance matching) between two material layers.

The diameter of the delay line element may be substantially identical to that of the piezo element.

Existing transducers featuring a delay line suffer from parasitic echoes (internal ringing or reflections) that produce several local blind spots with zero amplitude and also drastically reduce the sensitivity of the transducer. Moreover, the same negative effects occur when measuring non-invasively through material wall layers.

In the present invention, a circumference area, i.e. the outline area of the delay line material's cylindrical shape, may not be smooth. The outline area may be modified in such a way that undesired internal reflections inside the delay line material, which normally affect the performance of the delay line material and reduce the sensitivity of the transducer, are cancelled out. To this end, the outline area may be "non-smooth" e.g. terraced or stepped, or provided with bumps and crevasses at certain distances from the piezo element so that standing-wave phenomena (multiple reflections) causing blind spots are cancelled out. This in combination with the optimisation of the length and angle of the delay line may ensure that maximum acoustic energy is transmitted into the liquid of interest but also that the amplitude of the returning echo signals may not be attenuated as much as with existing delay line materials and transducers.

Moreover, a front surface of the delay line material (and hence the transducer front) may be further be configured to match the radius or internal curvature of a pipe. The curvature of the transducer front may thus match that of the pipe exactly but it may also differ slightly. A front surface with a curvature and the non-smooth circumference may have an additional advantage of producing a more focused beam with smaller beam diameter and a longer focal zone in front of the transducer thus resulting in much more accurate velocity measurements. It may also be possible to measure accurate velocities within the near-wall layer close to the pipe wall.

The housing may be a stainless steel cylinder or similar shape. The housing material and shape may be of composite type and may be configured to reduce temperature gradients and vibrations along the transducer axis.

DESCRIPTION OF PREFERRED EMBODIMENTS

In the following description, for purposes of explanation, numerous specific details are set forth in order to provide a thorough understanding of an embodiment of the present disclosure. It will be evident, however, to one skilled in the art that the present invention may be practiced without these specific details.

Figure 1:
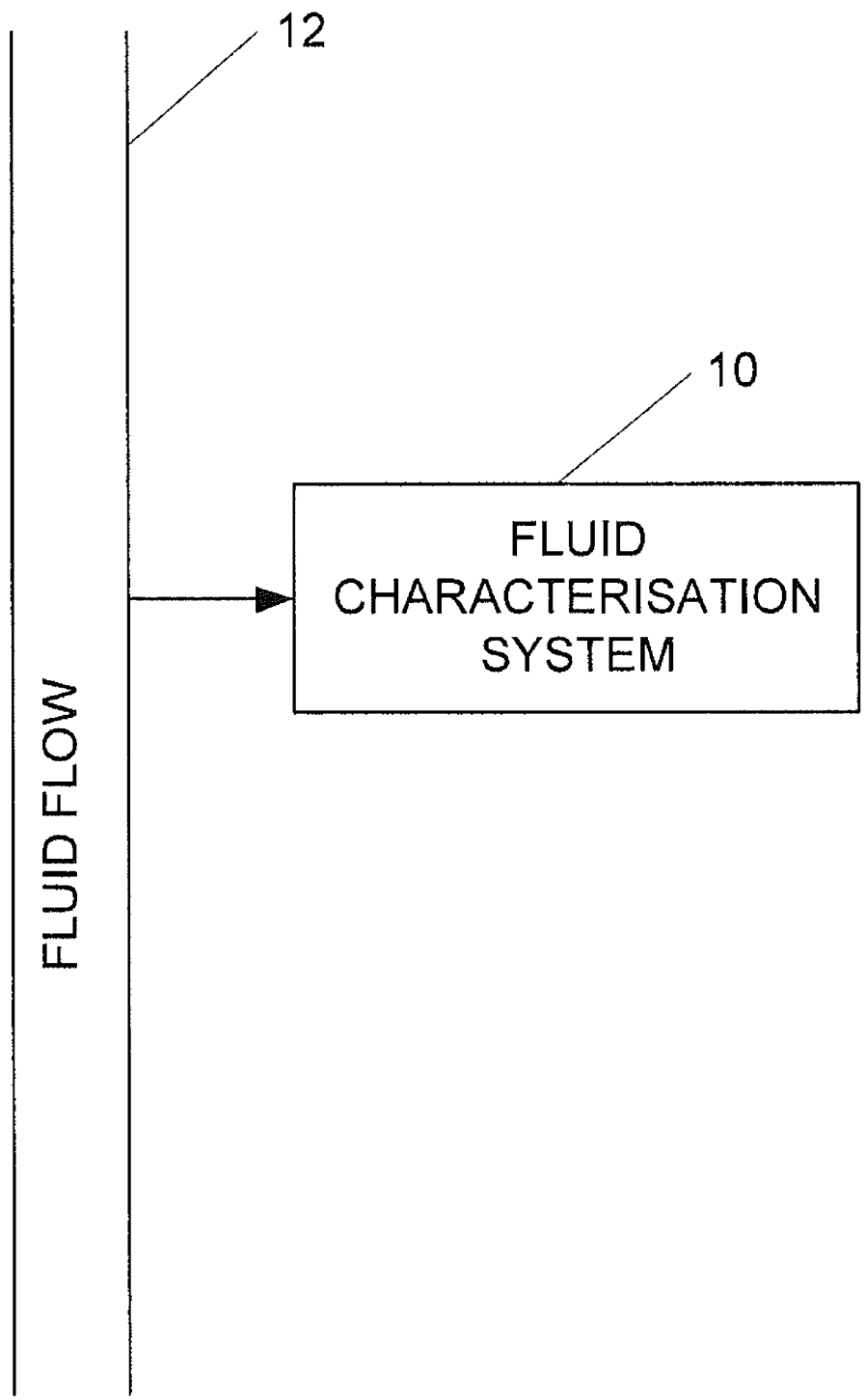
FIG. 1 shows a conceptual block diagram of a fluid visualisation and characterisation system in accordance with an example embodiment of the invention, operatively connected, in use, to a pipe of a pipe or fluid network or circuit.

Referring to FIG. 1 of the drawings a fluid visualization and characterisation system in accordance with the invention is generally indicated by reference numeral 10. At least a section of the system 10, for example, a measuring section thereof, is typically integrated with or connectable to a fluid network comprising means defining fluid flow paths for fluids flowing in the fluid network. The means are typically pipes 12 in a pipe network. Advantageously, the pipes 12 may form part of an industrial processing pipe network or circuit of the fluid network. The means could instead be other conduits capable of conveying fluids.

The system 10 also comprises electronics and signal processing elements to process the measurements obtained from the measuring section as will be discussed below. The electronics and signal processing elements need not be provided with the measurement section but may be remotely located therefrom and configured to receive measurement signals, or data indicative of or associated therewith, for example, wirelessly (e.g., via Bluetooth, Radio Frequency signals, via a wireless communication network, or the like) or via a hardwired connection.

The system 10 typically is configured at least to determine instantaneous radial velocity profiles and rheological properties of the fluid flow in the pipe 12 to which the system is connected to using Ultrasound Velocity Profile with Pressure Difference (UVP+PD)/Flow Depth (UVP+FD) techniques, as will be discussed in greater detail below.

Figure 2:
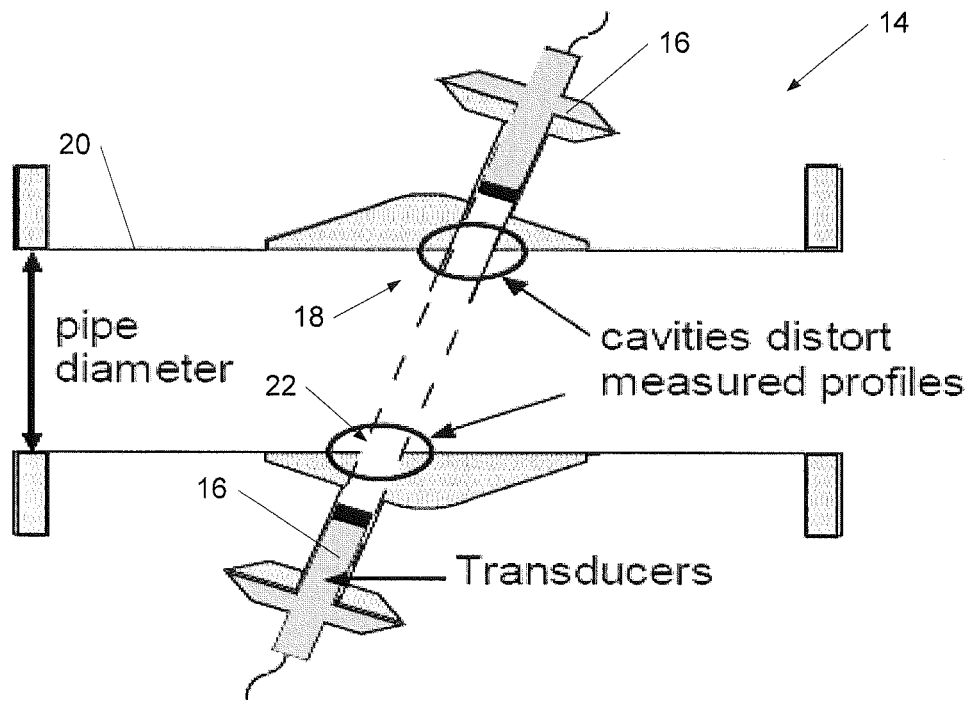
FIG. 2 shows a section through a conventional prior art system of the same general type as the present invention.
Figure 3:
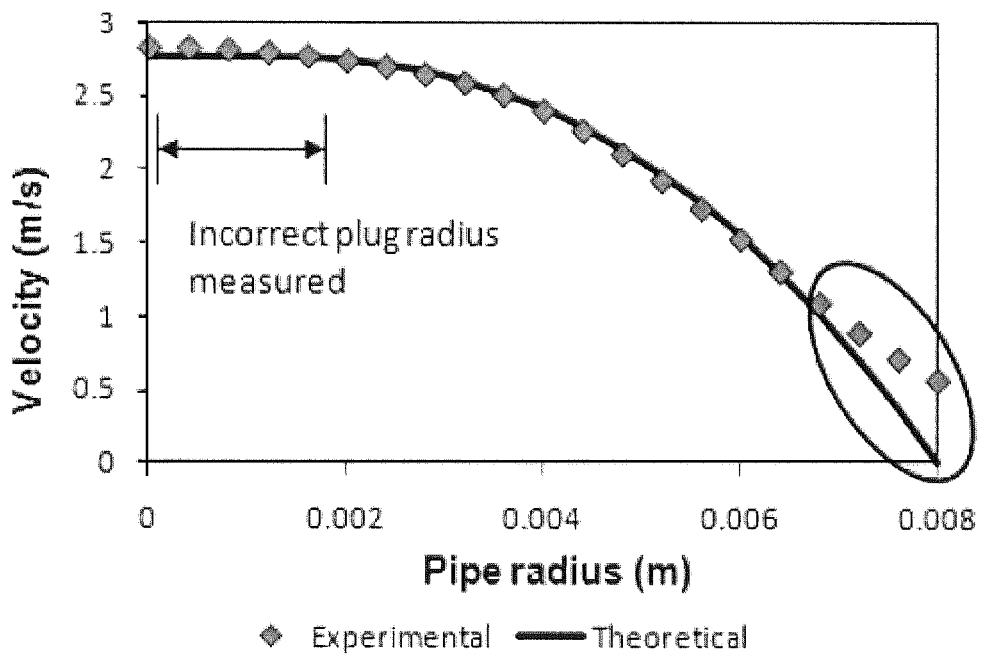
FIG. 3 shows a graph of a measured velocity profile of fluid flow in a pipe obtained using the system of FIG. 1.

As previously mentioned, referring now to FIGS. 2 and 3, conventional UVP+PD systems, systems 14 and methodologies make use of transducers 16 to transmit acoustic signals along a measurement line or axis into a fluid to determine characteristics thereof. In this regard, it will be appreciated that the fluids under investigation are subjected to, and most influenced by, the strongest shear in the near-wall region 18 (of pipes 20) with the highest velocity gradients. For rheological characterisation and monitoring of rheological properties, this near-wall region 18 with the highest velocity gradients is therefore of great importance and accurate velocity measurements must be made within this region of space.

Conventional UVP+PD systems make use of conventional, e.g., off-the-shelf transducers or simple transducer setups where the transducer is placed in direct contact with the fluid, e.g., a liquid (for maximum energy transfer) or through a thin transparent pipe to obtain measurements. However, due to the conventional transducer designs, the pressure field produced by the ultrasonic transducer is highly irregular from the transducer's surface and extending all the way up to the focal point thereof. This distance is usually quite long (typically around 17 mm for a 4 MHz transducer in water) and known as the near-field. Accurate velocity measurements are not possible in this region, which makes the transducer installation complicated and this has therefore limited the practical applicability of the UVP+PD method for industrial applications. To overcome this problem, simple flow adapter designs for transducer housings have been used that enable the transducer surface to be in direct contact with the test fluid, thus ensuring maximum ultrasonic energy transfer into the fluid system as well as eliminating any beam refraction.

However, the above-mentioned setup (illustrated in FIG. 2) leaves a cavity 22 before the wall interface 18 which causes measurement uncertainty due to fluid flow and increased velocities beyond the actual pipe wall (see FIG. 3). Furthermore, when measuring in more complex, industrial fluids, problems of particle sedimentation inside the cavities 22 cause velocity of sound and Doppler angle variations, which can distort the measured profile significantly. More consequences of particle build-up and density changes inside cavities 22 are the negative effects of temperature and fluid concentration gradients. This also causes velocity of sound variations and it has been shown that temperature gradients can cause errors in velocity profile estimation across the measurement line.

It is possible to measure through solid material layers and pull back the transducer from the liquid-wall interface, thus eliminating both the cavity- and the near-field problem. However, ultrasonic beam refraction and absorption causes errors in parameters such as the Doppler angle and sound speed, and this significantly reduces the penetration depth in attenuating fluids. It has been shown that the physical ultrasonic beam shape changes when measuring through material layers. If the acoustic properties of the pulses emitted and received by the transducer change, for example due to propagation through solid interfaces, more errors due to increased sample volume dimensions (widening of ultrasonic beam) are introduced into the velocity measurement, which leads to inaccurate results especially within the near-wall region which is of highest interest.

Velocity profiles are thus generally not measured with sufficient accuracy as a result of the effect of the finite sample volume characteristics and propagating through solid boundaries or wall material layers. The influence of the sample volume geometry and intensity will be described in greater detail below. Systems and methods for correcting measured velocities in the near wall region have previously been proposed, but with limited success.

Determining the actual wall interface (when measuring through material layers) or liquid-wall interface (when measuring with direct contact to the test fluid) is thus of great importance for rheological measurements. Due to the factors mentioned above, the determination of the interface is extremely complicated, especially when measuring velocity profiles with limited spatial resolution or when attenuation distorts the quality of near wall velocity data. It has been shown that by changing the wall position by less than 0.37 mm (or one channel) the rheological parameters determined using the UVP+PD method vary significantly. This is because the fluids under investigation are subjected to, and most influenced by, the strongest shear in the near-wall region with highest velocity gradients as described above.

The problem of uncertain wall positions has forced users to obtain rheological data of the test fluid using other methods such as off-line rotational rheometry in order to adjust wall interface positions that yield the correct fluid properties. However, this defies the purpose of the UVP+PD methodology for in-line rheometry, as it is desirable to have a complete UVP+PD based measuring system and methodology which can measure rheological properties without any a priori knowledge of the fluid characteristics.

Even when a correct wall position could be obtained, for example, by visual inspection or post data analysis, the theoretical fitting onto the experimental velocity profile is not straight forward and thus far users still need to adjust boundary conditions and initial estimates in order to obtain the correct rheological parameters. Different approaches have been attempted to the model fitting procedure, such as using polynomials of different orders, irrational power equations, splines or using different rheological models. However, even using these techniques, the problem of requiring knowledge of boundary conditions and initial estimates and/or fitting of different models forces the user to have knowledge of the fluid characteristics beforehand, which does not make this a viable independent rheometric measurement method. To overcome this problem a new generation of transducers is introduced in the present invention.

Figure 4:
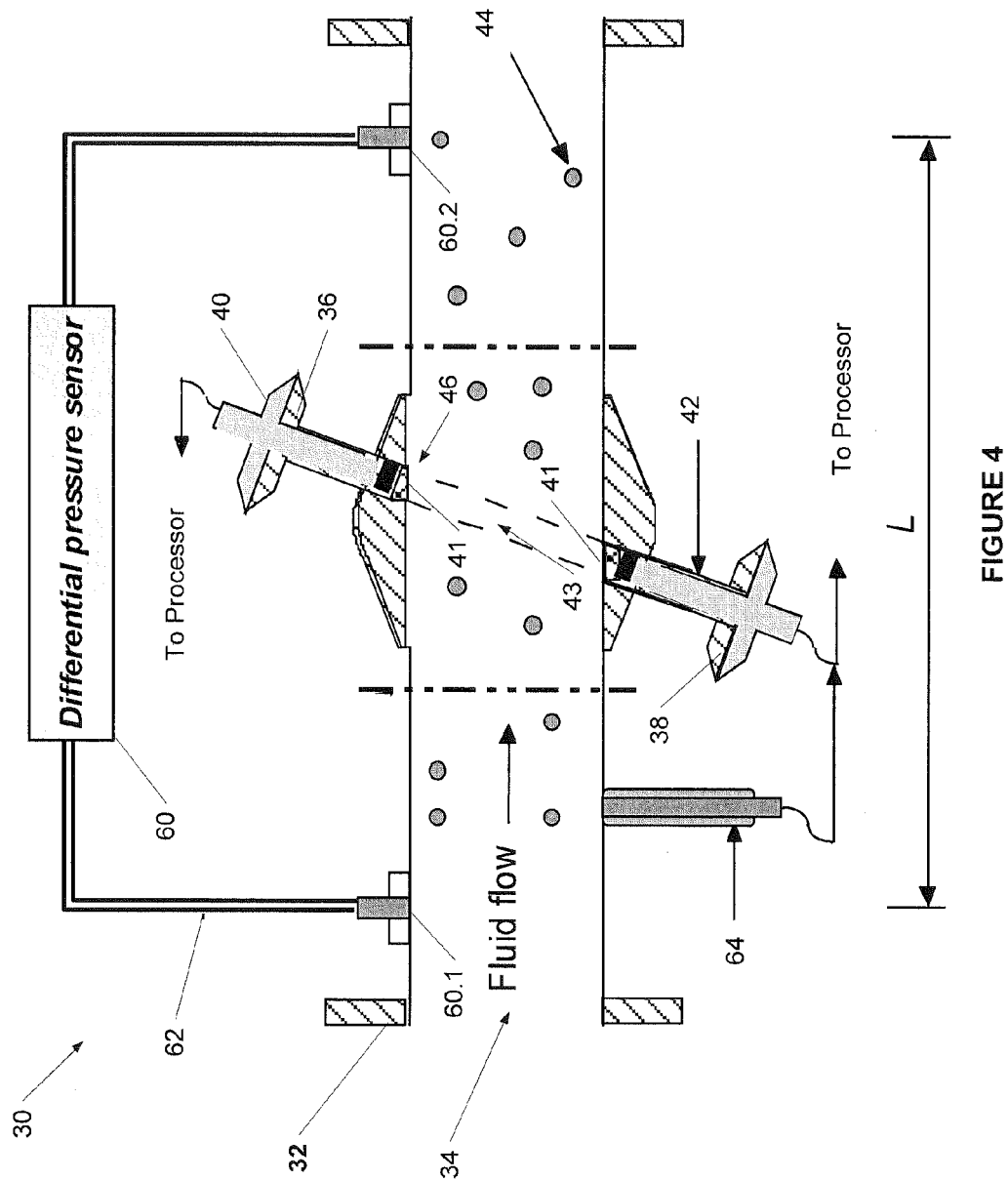
FIG. 4 shows a schematic, part-section, illustration of a fluid visualization and characterisation system, particularly a measuring section thereof, in accordance with an example embodiment.

Reference is made now to FIG. 4 of the drawings where a measuring or measurement section of the fluid visualization and characterisation system 10 in accordance with the present invention is generally indicated by reference numeral 30. It will be noted that the measuring section 30 may comprise some or all elements of the system 10 as will be described below or some of the components may be remotely located from the measuring section 30.

It will be noted that the system 10 makes use of the UVP+PD methodology which allows the determination of rheological parameters by combining Ultrasonic Velocity Profiling (UVP) with Pressure Difference (PD) measurements. It is used for in-line, non-invasive rheological characterisation of opaque complex fluid systems.

The measuring section 30 of the system 10 comprises a housing 32 defining a fluid flow passage 34, e.g., a hollow cylindrical fluid passage for passage of fluid therethrough; a first transducer port 36 located adjacent the passage 34; and a second transducer port 38 also located adjacent the passage 34 such that the first and second transducer ports are in-line and opposite each other, spaced apart by the passage 34.

In one example embodiment, the housing 32 is a flow adaptor configured to be fitted onto a pipe system such that the fluid flow passage 34 fits snugly onto a pipe of the pipe system. However, it will be appreciated that the housing 32 may be adapted to be installed integral with a pipe system such that the fluid flow passage 34 is in flow communication with the pipe system.

The pipes in the pipe system may be cylindrical pipes. However, the present invention is not limited thereto and may take various geometric, hollow, shapes. For ease of explanation, "pipe" in the context of the present description will be understood to mean a hollow cylindrical member having a fluid/liquid substance flowing there through, the characteristics of which is advantageously determined by the system 10 as herein described.

In any event, in order to achieve desired functionality, the system 10, particularly the measuring section 30 thereof, comprises a first delay line transducer 40 configured to emit a high frequency signal into the fluid flow in the passage 34. The high frequency signal is an acoustic signal, typically an ultrasound signal.

The delay line transducer 40 comprises a delay line 41 material for generating desired ultrasound signals as will be discussed below.

The measuring section 30 also comprises a receiver 42 configured at least to receive reflection signals, the reflection signals being reflection/s of the ultrasound signal emitted by the first delay line transducer 40 from reflector/s 44 in the fluid flow. The receiver 42 may comprise any circuitry etc. to received reflection signals. However, the receiver 42 comprises a second delay line transducer 42. The first transducer 40 may be receivable in the first transducer port 36 of the housing 32 and the second transducer 42 may be receivable in the second transducer port 38 such that the first transducer 40 and the second transducer 42 are directed or in line with each other along a measuring line or a beam axis 43. The system 10 may comprise a plurality of delay line transducer pairs. However, only one is illustrated for ease of illustration.

In one example embodiment (mentioned below), the first transducer 40 may also comprise the receiver 42 if necessary or expedient to do so such that it can emit or transmit the ultrasound signal and receive the reflection signal accordingly. In this example embodiment, the housing 32 may be adapted accordingly.

The second transducer 42 could also easily emit the ultrasound as mentioned above, which the first transducer 40 could receive in a similar fashion as the second transducer 42. However, for ease of explanation, reference will be made to the example embodiment where the first transducer 40 is configured to emit ultrasound waves and the second transducer 42 is configured to receive reflections as hereinbefore described.

It will be appreciated that good and stable positioning of the ultrasound transducers 40, 42 is essential for the successful measurement of velocity profiles (discussed below).

The transducers 40, 42 are installed flush with the pipe wall 46, thus leaving no cavity between the transducers 40, 42 and wall interface. The elimination of the cavity as previously mentioned allows for more accurate velocity profile measurements as no unrealistic flow is possible beyond the actual pipe wall interface. This also solves the problem of sedimentation and clogging (when testing viscous fluid suspensions) of the cavities ahead of the transducers also as previously mentioned.

It should be noted that the terms "delay line", "acoustic wedge", "acoustic couplant", etc. are sometimes used for a special type of transducer or transducer accessory designed for non-destructive testing. However, in the case of the present example embodiment the replaceable "delay line" material is used to delay the emitted ultrasound signal so that it can be used to obtain optimum acoustic beam properties, such as beam forming, beam focusing, acoustic coupling, impedance matching, beam path, and sensor protection.

An "acoustic wedge" on the other hand is designed, for example, to generate or eliminate different types (e.g. shear/longitudinal waves) of wave in any solid or semi-solid materials that could be used for non-invasive measurements. An "acoustic couplant" is defined as a material used to ensure maximum energy transfer between the ultrasonic transducer and the material.

It should be noted that in the context of this invention the term "delay line" material could mean an "acoustic wedge", "acoustic couplant", or a combination thereof that has multiple functionalities such as beam forming, beam focusing, acoustic coupling, impedance matching, desired beam path generation and/or elimination and sensor protection.

In the present invention, the delay line 41 is constructed from a suitable material to achieve several ends. Firstly, the delay line 41 is used for beam forming and the material from which it is constructed from contains the acoustic near-field distance of the transducer 40, 42 (in which the acoustic pressure is non-uniform and goes through a series of maxima-minima). The delay line material is typically made of one or a combination of Polycarbonate (PC), Parylene, Epotek, and Rexolan or similar materials. The acoustic properties of the material of the delay line 41 are optimised so that the acoustic impedance and the velocity of sound are as close as possible to that of water (or other industrial fluid) as well as pipe walls (e.g. stainless steel). The delay line thus provides optimal acoustic coupling between the transducer and the fluid under investigation.

Secondly, this delay line 41 is fixed ahead of the transducer 40, 42 as an integral part of the design and is flush with the pipe wall 46. The delay line material is either glued (using appropriate glue) or die cast directly to a front matching material of the transducer or the piezo element, or linked to the transducer using acoustic coupling materials.

It will be noted that the matching material may form part of an ultrasonic matching layer. This layer may be a passive layer, which is fixed to the front face of an ultrasonic transducer in order to improve the coupling of energy to and from the transmission medium. Under narrow-band conditions, coupling is maximised when the thickness of the matching layer is equal to one quarter of the wavelength (or an odd multiple of a quarter wavelength).

In addition, the transducer 40, 42 may also comprise a backing material which is most commonly a highly attenuate and very dense material and is used to control the vibration of the transducer crystal/piezo element by absorbing the energy that radiates from a back face of the piezoelectric element. When the acoustic impedance of the backing material matches that of the piezoelectric crystal, the result is a highly damped transducer with excellent resolution. By varying the backing material in order to vary the difference in impedance between the backing and the piezoelectric crystal, a transducer will suffer somewhat and resolution may be much higher in signal amplitude or sensitivity.

A tip portion of the delay line 41 may have different shapes, e.g. angle and curvature may be varied so that the thereof geometry exactly matches that of the radius or the internal curvature of the pipe wall 46 to ensure no distortions to the streamlines (velocity gradients) in the near-wall layer. The curvature of the front surface of the delay line 41, or tip portion, may match that of the pipe exactly but it may also differ slightly. A front surface with a curvature and the non-smooth circumference area has the additional advantages of producing a more focused beam with smaller beam diameter and a longer focal zone in front of the transducer thus resulting in much more accurate velocity measurements. It is also possible to measure accurate velocities within the near-wall layer close to the pipe.

Thirdly, the transducer 40, 42 is configured so that the focal point of the ultrasonic beam, with maximum acoustic pressure is located exactly at the liquid-wall interface thereby, advantageously, enabling accurate measurements directly at a front section of the transducer 40, 42. To this end, it will be understood that the length of the delay line is linked to a quarter wave length, as described above, and the ultrasound frequency of the transducer so that the focal point with maximum acoustic pressure is located at the front surface of the tip portion of the delay line 41.

It will be noted that the circumference area i.e. the outline area of the delay line material's cylindrical shape is not smooth. The surface area is modified in such way that undesired internal reflections inside the delay line material, which normally affects the performance of the delay line material and reduces the sensitivity of the transducer are cancelled out. This in combination with the optimisation of the length of the delay line ensures that maximum acoustic energy are transmitted into the liquid of interest but also that the amplitude of the returning echo signals is not attenuated as much as with existing delay line materials and transducers.

Moreover, in the present invention, the design of the delay line 41 plus transducer components are optimised so that maximum energy transfer between the ultrasonic transducer 40, 42 and the fluid is ensured but also so that parasite echoes and "blind spots" along the transducer beam axis are avoided. This is achieved by optimisation of the geometry, length, shape and acoustic properties of the delay line material 41, piezo active element of the transducers 40, 42, backing material, front and wear plate of the transducer 40, 42, etc. some of which is herein before described. The length of the delay line 41 is linked to multiples of the quarter wave length and is carefully chosen to avoid induced reflections that would reduce the efficiency of the transducer 40, 42.

It will be appreciated that the piezo element of the transducer is a piezoelectric ceramic element crystal for producing and receiving high frequency signals. The piezo element is typically made of $PbTiO_2$. Special doping of lead zirconate-titanate ceramics of the piezo elements make it possible to adjust individual piezoelectric and dielectric parameters as required. The diameter, length and shape etc. of the piezo element typically determines the frequency and acoustic properties of the transducer.

The entire transducer 40, 42 including the delay line 41 and the tip section thereof is further optimised to work under real industrial processing conditions over a wide pressure and temperature range and also to resist wear from solid, abrasive particles suspended in the liquid. The housing may be a stainless steel cylinder or similar shape. The housing material and shape may be of composite type and may be configured to reduce temperature gradients and vibrations along the transducer axis.

In certain example embodiments, the delay line transducer may feature an additional front surface material which is fixed to the delay line material. This material may be an acoustically matching ceramic material and it is used to protect the transducer from wear, abrasive or corrosive fluids and materials and high temperatures by providing a buffer zone.

In this regard, the housing material and shape are chosen so that temperature gradients along the transducer are eliminated e.g. by using an insulating ceramic layer.

In any event, the current limitations regarding temperature and pressure are 0-150° C. and 0-30 Bar (0-3000 kPa), but this can be extended depending on the application. E.g. when using non-invasive delay line material.

Although discussed above, reference will now be made to FIGS. 5 to 7 of the drawings where more specific example embodiments of delay line transducers 40, 42, are illustrated. The delay line transducers 40, 42 shown in FIGS. 5 and 6 typically comprise at least piezo elements 48 disposed in a housing 50 with the delay line materials 41 attachable adjacent to the elements 48. The delay lines 41 may be removably attachable to the end sections of the transducers 40, 42 or may be integral therewith as previously described. For pipe flow measurements transducers 40, 42 with a central basic frequency of 2 MHz (FIGS. 5 and 6) and a beam diameter of 10 or 5 mm are normally used in order to obtain a good compromise between spatial resolution, which is due to their short wavelength, and penetration depth (less attenuation).

When the ultrasonic frequency is defined, a diameter of the piezo element 48 may be optimised, taking into account the following points: a small diameter means a less sensitive transducer 40, 42; a large diameter means a less diverging beam, which implies a smaller sampling volume; a large diameter means a longer near field, which means that the measurement close to the transducer 40, 42 will be affected by the oscillation of the ultrasonic pressure field and this must be compensated for by the use of a longer delay line 41 as hereinbefore mentioned. A diameter of the housing 50 is typically between 8-12 mm and the length thereof is 20-100 mm.

Figure 5:
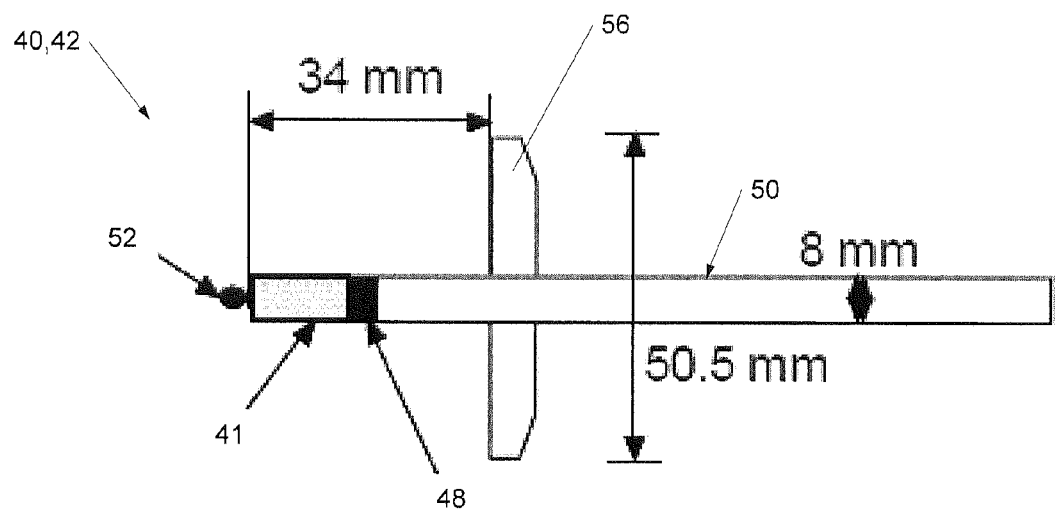
FIG. 5 shows a schematic drawing illustrating a 2 MHz delay line transducer with no angle compensation in accordance with an example embodiment.
Figure 6:
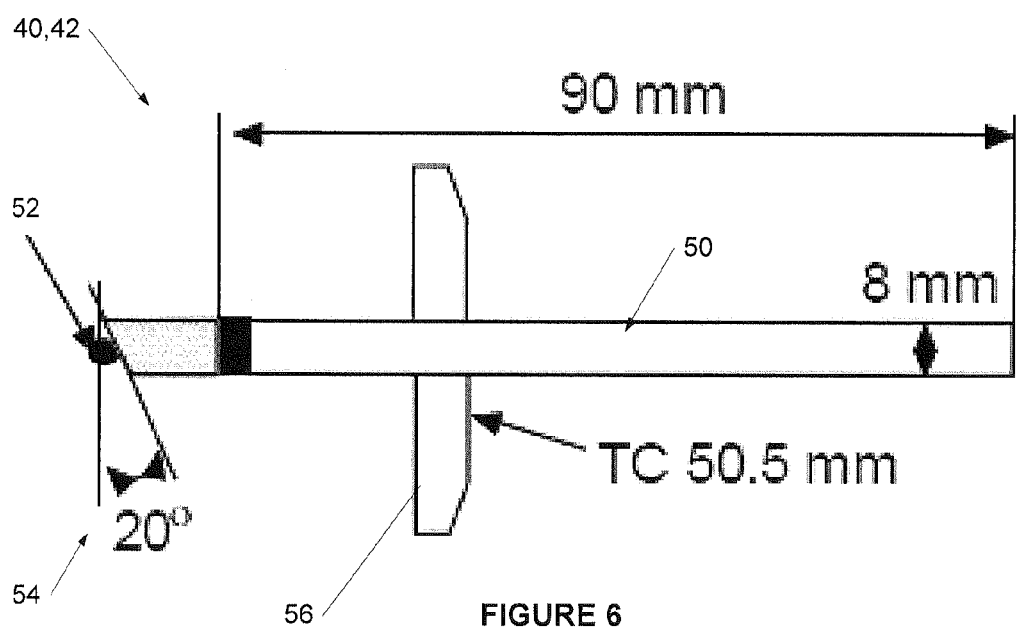
FIG. 6 shows a schematic drawing illustrating a 2 MHz delay line transducer with angle compensation in accordance with an example embodiment.

It will be noted that focal points 52 of the transducers 40, 42 are illustrated in FIGS. 5 and 6. Also illustrated in FIG. 6 is the angle compensation 54 for transducers 40, 42 having angle compensation. The angle compensation can be selected to be any angle, depending on the pipe diameter, flow rate and fluid characteristics angle of transducer installation, in the present example, an installation angle of 20 degrees was used. The angle may be determined experimentally. However, for small pipe diameters the angle should be close to 90 degrees with respect to lateral in order to avoid averaging effects across the velocity profile gradient.

In Table 1 below, typical geometric dimensions and major acoustic parameters are given for a 2 MHz transducer 40, 42 in accordance with the above description with reference to FIGS. 5 and 6.

TABLE 1

| Delay line transducer specifications - 2 MHz (FIGS. 5 and 6) | | | | | | |
|---|---|---|---|---|---|---|
| Centre frequency (MHz) | Delay line characteristics | Delay line length (mm) | Active diameter (mm) | Housing diameter (mm) | Overall length (mm) | Divergence half-angle (deg) | Installation |
| 2 | Acoustic impedance matching for industrial suspensions 1400-1700 m/s) | 14 | 5 | 8 | 90 | 2.2 | TC 50.5 mm disc, distance from TC plate to transducer front 34 mm |

It will be noted that the ultrasonic transducers 40, 42 have a frequency range of 0.5-15 MHz, and as described above are designed to operate in both transmitting and/or receiving mode, individually or in pairs (e.g. the first transducer 40 operating in a dedicated emitting mode and the second transducer 42 operating in dedicated receiving mode, or vice versa). The transducers 40, 42 can work both in continuous and pulsed excitation mode and produce short or long bursts of ultrasound, typically of sinusoidal or square wave type but also other waveforms such as chirps, if desired. In addition to being installed and operated used both individually and in pairs, the transducers 40, 42 may be provided in different configurations (opposite to one another, V- and Z-, ring-configuration, etc.) to measure both in the direction of the flow and opposite the flow direction. The present invention also covers a linear/phased array transducer design equipped with a delay line 41 as described above.

Furthermore, the transducer 40, 42 may be optionally fitted with, for example, a triclamp disc 56 (see Table 1 and FIGS.

5 and 6) for easy and hygienic installation of transducers 40, 42, which is usually a prerequisite in applications found in the food or pharmaceutical industries. The transducer could also be optionally fitted with a clamping system for accurate positioning of delay line transducers (when using the non-invasive sensor setup).

However, more importantly, in the present invention, the transducer 40, 42 is equipped with an optimised delay line 41 and disc 56 for easy and hygienic installation of transducers 40, 42, allows exact positioning of the transducer 40, 42 and also a fixed wall position. This ensures and allows not only accurate measurements directly from the transducer front and within the gradient layer near the wall 46, but also accurate rheological characterisation and determination of rheological parameters by eliminating the uncertainty in determining the wall positions as will be described below.

Figure 7:
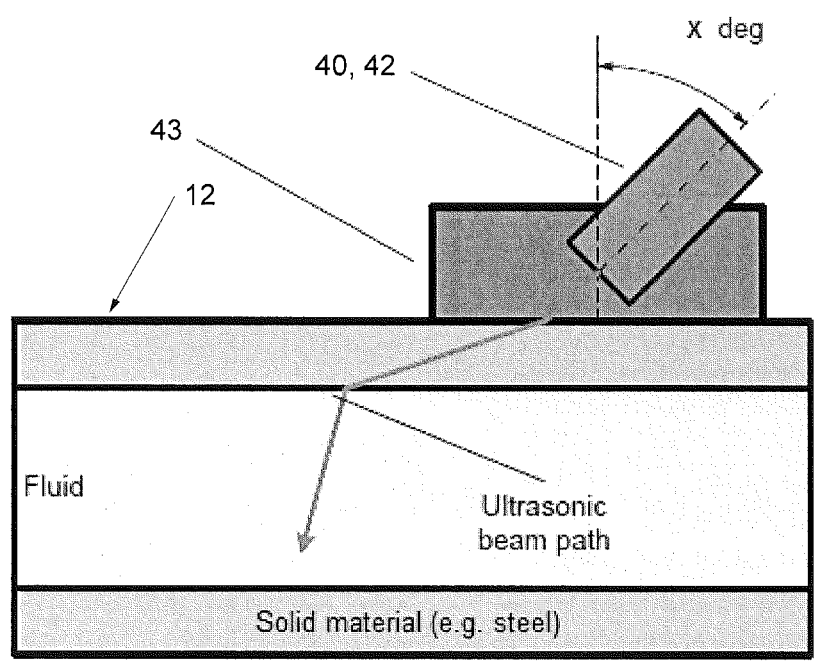
FIG. 7 shows a simplified schematic diagram of a transducer with an associated delay line element in a non-invasive sensor configuration.

An alternative embodiment of a non-invasive measurement setup is shown in FIG. 7. For purposes of the present invention the term "non-invasive" setup indicates that no part of the transducer or delay line material is in contact with the test fluid. In other words, the transducer and delay line element are located externally of the pipe or other means 12 in which the fluid to be characterised is conveyed.

A suitably shaped element or block 43 of delay line material is used in order to acoustically couple the transducer 40, 42 with a solid material layer (e.g. a pipe wall). As previously described, the delay line material should provide optimum acoustic beam properties (such as beam forming, focusing, coupling, impedance matching, optimum beam path through material layers and into the fluid medium as well as sensor protection). As previously described, the delay line is designed to generate or eliminate different types of waves in any solid or semi-solid materials that could be used for non-invasive measurements.

The block of delay line material could either be an integral part of the transducer and/or the material wall layer (e.g pipe wall) or a clamp-on device, for example. It should be noted that in FIG. 7 the direction of the beam path is just an illustration.

Returning to FIG. 4, it will be appreciated that the system 10, particularly the measuring section 30 thereof, also comprises a differential pressure sensor 60 for wall shear stress measurements. The sensor 60 is configured to measure a pressure differential between two points along the fluid flow 34 by way of membranes 60.1 and 60.2. To this end, the sensor 60 may also comprise a vacuum tube 62 filled with pressure transmitting fluid. Since the velocity of sound in a fluid medium can significantly change with variation in fluid temperature, the system 10 may also comprise a temperature sensor 64. It will be noted that when fluid rheology is of interest, temperature of the fluid can also play a significant role in the viscous properties of a particular fluid. The measuring section 30 of the system 10 is designed for simultaneous measurements of velocity profiles and acoustic properties in-line.

Figure 8:
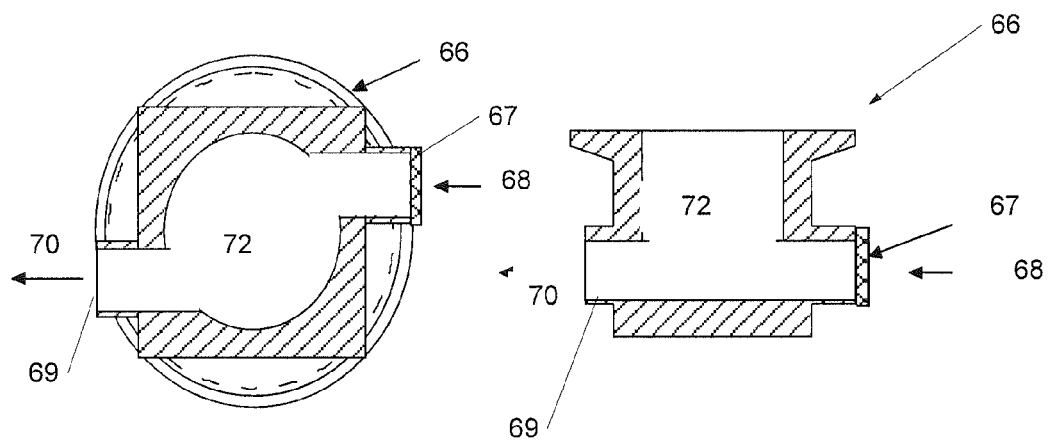
FIG. 8 shows a schematic drawing illustrating a sectional top view and a sectional side view of a pressure adaptor in accordance with an example embodiment.
Figure 9:
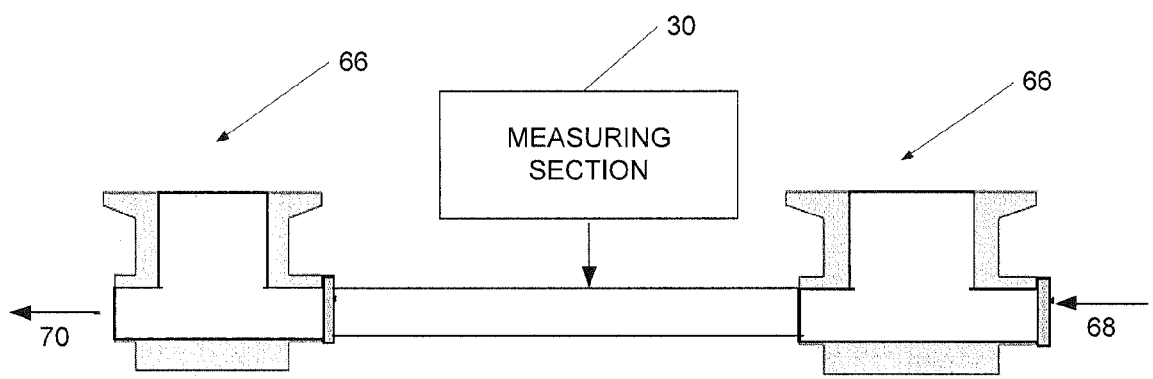
FIG. 9 shows a schematic drawing illustrating a system, particularly a conceptual block of the measuring section thereof, connected between two pressure adaptors of FIG. 8.
Figure 10:
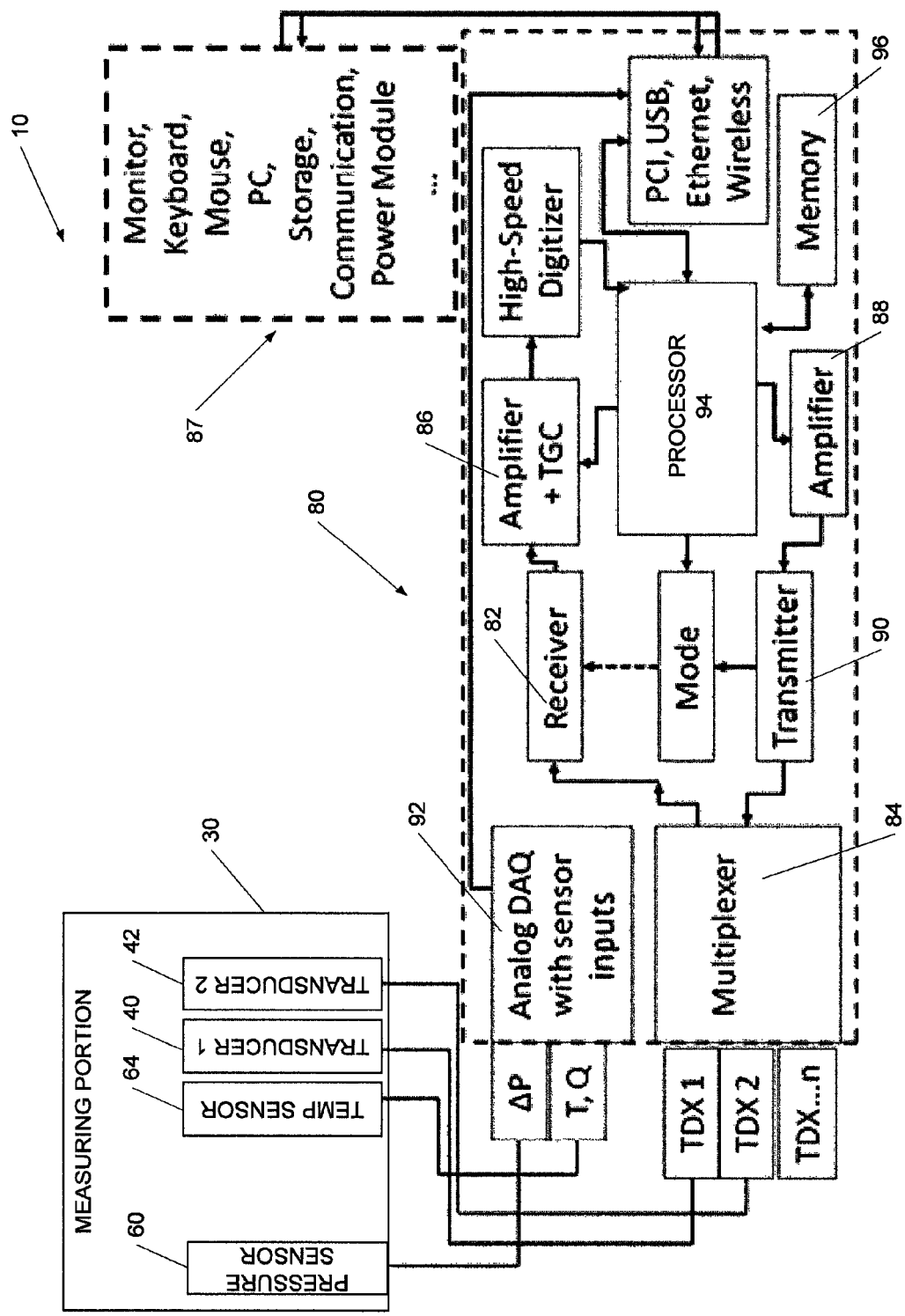
FIG. 10 shows a schematic drawing of a section of the fluid visualization and characterisation system, illustrating the electronic/hardware components thereof in greater detail.

The system 10 may further comprise or the measuring section 30 may be in flow communication with pressure flow adapters 66 (FIGS. 8 and 9). The pressure flow adapter 66 may be connected upstream and downstream of the measuring section 30 for more accurate pressure drop measurements (FIG. 10). The pressure flow adapter 66 may comprise an inlet port 67 to receive an inlet fluid flow 68 and an outlet port 69 to provide an outlet 70 of the fluid flow. The inlet port 67 and the outlet port 69 may be spaced by a cylindrical flow chamber 72 which are not in line with each other. The asymmetrical configuration of the inlet and outlet ports 67, 69 ensure a continuous steady flow of fluid to the measuring section 30. It will be appreciated that in certain example embodiments, the pressure sensor 60 requires that the pipe is fully filled with fluid and a steady flow past sensor 60 membranes 60.1 and 60.2 in order to measure pressure differences therebetween accurately. Poor sensor housing design in combination with small changes in pressure or errors in measurements could thus result in erroneous rheological properties determined by the system 10.

As illustrated in FIG. 9, adaptors 66 may be provided upstream and downstream of a fluid flow and may be interconnected by way of a pipe. The pipe may comprise the measuring section 30 of the system 10 or the measuring section 30 may be attachable onto the pipe.

In any event, in addition to simply obtaining measurements by way of the measurement section 30, the system 10 achieves functionality as hereinbefore mentioned at least by making use of a pulsed ultrasound velocity profiling technique (UVP) to determine at least velocity profiles of fluid flow 34. This technique relies on determination of the frequency shift or time-domain shift of backscattered signals reflecting of particles or bubbles in a flowing liquid. This shift is obtained in real-time as a function of spatial range for a large number of spatial positions/times. From these measurements, an instantaneous velocity profile of the fluid flow 34 is determined. It will be appreciated that from a single velocity profile at a simultaneously measured pressure gradient, the system 10 may determine fluid rheological properties over shear rates ranging from zero at a center of the pipe to the maximum shear rate at the pipe wall 46.

To this end, reference is made to FIG. 10 of the drawings where the system 10 of the present invention is illustrated. In addition to the conceptual block of the measuring section 30, FIG. 10 illustrates the system 10 also comprising electronics and signal processing elements 80 to receive and process measurement signals from the sensors and transducers 40, 42 of the measurement section 30 via a hard-wired connection or wirelessly (e.g. the measurement section 30 may comprise a wireless transmitter to transmit measured signals to a suitable receiver) thereby to provide the system 10 with the functionality desired. The electronic and signal processing elements 80 and the measuring section 30 typically make up the system 10. As previously mentioned, elements 80 may be located at the measuring section 30. However, for ease of illustration and explanation, these are described separately with the elements 80 being remote from the measuring section 30, despite being communicatively coupled therewith, for example, wirelessly as hereinbefore mentioned.

In certain example embodiments the elements 80 are provided in a personal computer (PC), laptop, or other suitable computing device. However, in the present example embodiment, the elements 80 may be interfaced with these types of computing devices but form part of a separate system 10.

The electronics and signal processing elements 80 are conveniently configured to control the components of the measuring section 30 as well as to process received measurements as described herein. It will be understood by those skilled in the art that functionality of some of the electronic and signal processing elements 80 may be achieved in a plurality of different ways. However, this should not detract from the spirit of the invention described herein.

In particular, the system 10 comprises a pulse-receiver unit 82 to receive signals or pulses from one or both of the transducers 40, 42, particularly transducer 42 (for ease of explanation). The unit 82 is equipped with a multiplexer 84 and hardware based variable gain and Time-Gain-Compensation (TGC) devices 86 that can be programmed by a user so that gain curves of several different types can be used by the system 10.

In one embodiment, the system 10 comprises an arbitrary waveform or signal generator (AWG), not shown, which produces a sequence of signals or pulses at a pulsed repetitive frequency (PRF). For ease of explanation, signals and pulses may be considered to refer to the same.

An advanced signal generator may be provided for sophisticated shaping of the PRF waveform signal to control the shape, amplitude, duration and frequency of the output signal. The output signal is amplified by a power amplifier 88 and then passes through a transmitter 90 and the multiplexing unit 84 before it is converted into an acoustic signal by the transducer 41.

The signal frequency in the present invention is preferably in the Megahertz range of 0.1-50 MHz, with a pulse width ranging from 0.5 up to 20 cycles per pulse (example, a sinusoidal signal) with the pulse repetition rate greater than twice the maximum expected Doppler frequency shift (Nyquist theorem). The "off" period between pulses is long enough to permit any reverberation and echoes from one pulse to die out before the subsequent pulse is transmitted.

The electronics and signal processing elements 80 are designed so that the transducers 40, 42 can work both in continuous and pulsed excitation mode and produce short or long bursts of ultrasound, typically of sinusoidal or square wave type but other waveforms such as chirps can also be used by the present invention. After short emission/transmission of ultrasound wave along the measurement axis (through the fluid), the electronics 80 switches to receiving ('listening') mode. When the ultrasound pulse hits a small particle 44 in the liquid/fluid, part of the ultrasound energy scatters on the particle 44 and echoes back. The echo or reflection signal reaches the receiving transducer 42 after a time delay. If the scattering particle 44 is moving with a non-zero velocity component into the acoustic axis of the transducer 42, Doppler shift of the echoed frequency takes place, and the received signal frequency becomes 'Doppler-shifted' by the frequency equal to the Doppler shift frequency.

The transducer 42 detects acoustic energy or the reflection signal/pulse from small travelling, reflecting particles or bubbles 44 in the flowing liquid. A data acquisition block receives the delayed reflection signal and a timing-circuit is used for "time-gating" the received signal, so that the sample regions may be either adjacent or spaced-apart. Only the signal that corresponds to a selected range of acoustic travel times is selected for processing. In the preferred embodiment, multiple sample regions are processed in parallel but only a single sample region can also be processed at a time. A delay and range-gate can be adjusted to obtain the frequency shift or time-domain shift in one or several sample regions, determined by the control software (discussed below).

It will be understood that the acoustic signal or pulse received by the receiving transducer 42 is converted into an electric signal that is buffered and amplified by a receiving amplifier 86 equipped with a Time-Gain-Compensation (TGC) device. In the preferred embodiment, the received RF signal can be demodulated and low-pass filtered to provide a frequency shifted signal for velocity estimation but the system 10 in the present invention also high-pass filters the received signal to remove any low-frequency signal caused by e.g. walls 46 and reverberation of the pipe. The system 10 in the present invention also low-pass filters the received signal to remove undesired high-frequency components. It will be noted that the term RF (Radio Frequency) here is commonly used to describe unprocessed 'raw' data in the ultrasonics field, sometimes this abbreviation is also used to denote wireless transfer of data in electronic communication applications.

Raw RF echo data obtained from each pulse is recorded, which is used in velocity estimation algorithms discussed below, but also for visualisation and monitoring of the spectral content of the Doppler shift frequencies obtained using Fast Fourier Transform (FFT) algorithms.

If the electronics 80 in the present invention succeeds to measure the delay and frequency shift or time-domain shift of backscattered signals reflecting off particles 44, it is then possible to calculate both position and velocity of a particle. Since it is presumed that scattering particles are small enough to follow the liquid flow, it is also presumed that the system 10 is operable to establish a fluid flow component in a given space point. The complete instantaneous velocity profile may thus be obtained in real-time using several different velocity estimation algorithms (time domain and frequency domain) at the same time for enhanced accuracy and quality of the measured velocity profiles (discussed below). It will be noted that although the system only measures the raw RF data, the determined velocity profiles from the echo data are the measured profiles using the present system. The preferred embodiment further contains an analog data acquisition module (e.g., an analogue to digital module, DAQ) 92 with sensor inputs and signal conditioning modules for simultaneous receiving of measurements of pressure difference, temperature, volumetric flow rate, etc. from the appropriate sensors in the measurement section 30. In this way, the system 10 is configured to combine a measured pressure drop, which is used to determine the shear stress profile with the corresponding shear rate profile obtained from the velocity profile to determine the rheological properties, as described further below.

In addition, the system 10 is configured to determine the instantaneous, average velocity of sound in the fluid along each transducer beam or measurement axis 43 using e.g. time-of-flight measurements between the two transducers 40, 42. Attenuation of the acoustic energy of ultrasound in the fluid along each transducer beam axis 43 is also measured. This information is used to calculate e.g. the radial position of the various sample regions, the concentration of solids and the volumetric flow rate, which can also be obtained from integration of the measured velocity profiles and by transmit-time (sing-around) differential method.

It will be appreciated that the method may use transit-time differential methods by using two transducers mounted at opposite sides (as with the present invention) and using one transducer to transmit and the other to receive and vice versa, thus recording time-of-flight measurements with and against the direction of fluid flow. This information may be used to determine the volumetric flow rate if a flow velocity profile is assumed for the particular fluid under investigation. It will be noted that the combination of the velocity profile integration and transit-time method may be used in order to obtain more accurate flow rates.

The system 10, particularly the electronics and signal processing elements 80, advantageously comprises a processor 94 for directing the operation of the system 10, especially the elements 80. The electronics and signal processing elements 80 may include a machine-readable medium or memory 96, e.g. memory in the processor 94, main memory, and/or hard disk drive, which carries a set of instructions or control software as mentioned above to direct the operation of the processor 94. It is to be understood that the processor 94 may be one, more, or a combination of microprocessors, controllers, digital signal processors (DSPs), field programmable gate arrays (FPGAs), or any other suitable computing devices, resources, hardware, software, or embedded logic.

The instructions may be control software or embedded control software.

Figure 11:
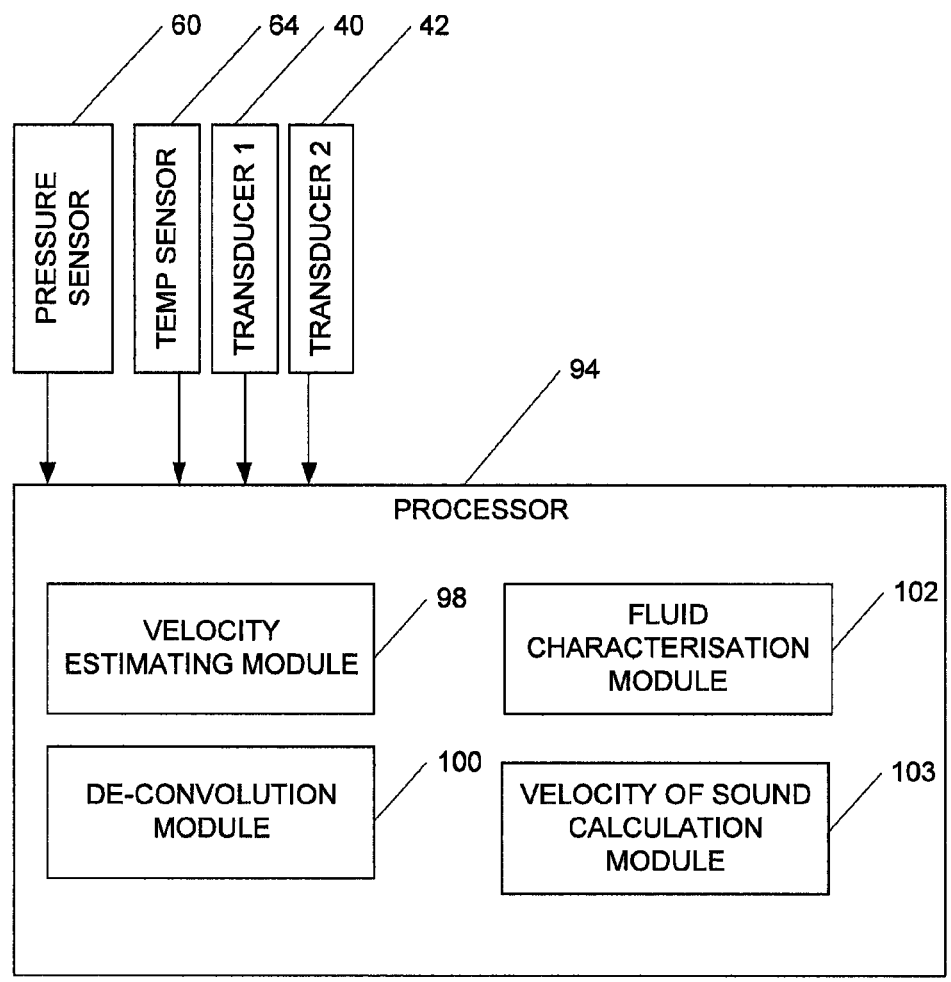
FIG. 11 shows a schematic drawing of a section of the fluid visualization and characterisation system, particularly the processor, illustrating the functional components thereof.

With reference to FIG. 11 of the drawings, the processor 94 typically comprises one or more modules which correspond to the functional tasks to be performed by the processor 94. In this regard, "module" in the context of the specification will be understood to include an identifiable section of code, computational or executable instructions, data, or computational object to achieve a particular function, operation, processing, or procedure. It follows that a module need not be implemented in software; and in other example embodiments (not discussed further) a module may be implemented in software, hardware, or a combination of software and hardware. Further, the modules need not necessarily be consolidated into one system but may be spread across a plurality of systems.

It will further be noted that instead, or in addition, to certain components of the electronics and signal processing elements 80 being provided as discrete components and described as such, the processor 94 may also comprise some of these components as code modules are hereinbefore described, for example, the various filters described herein.

In any event, the processor 94 comprises a velocity estimating module 98 configured to apply one or more velocity determining algorithms to the received reflection signals, or data indicative thereof, to determine the velocity profile of fluid flow 34 in the pipe. The velocity estimating module 98 may be configured to apply simultaneously a plurality of velocity determining algorithms to determine the velocity profile. The velocity determining algorithms may be time domain and frequency domain algorithms which are applied at substantially at same time for enhanced accuracy and quality of measured velocity profiles (spectral information and velocity estimation).

Determining or estimating velocity profiles of flowing fluids from the returning/sampled echo signals are known, for example, the Burg algorithm and a complex FFT method. The Burg algorithm (autoregressive method) provides a power spectrum with less variance (more precision in Doppler frequency estimation). However, when the full spectral profile is considered it is ideal to have access to both methods, since the FFT can be used for detailed spectral analysis of the Doppler signals.

Determining the correct Doppler frequency from a signal with a broad spectral spread and low signal-to-noise ratio can be extremely complicated and thus scientists are always interested in alternative signal processing techniques. Time domain signal processing techniques have been found to perform well in a wide range of signal-to-noise ratios than when compared to standard FFT methods.

Time domain algorithms may be separated into (i) phase-shift estimators that employ autocorrelation techniques of the baseband signal and (ii) time shift estimators that use frequently cross-correlation of the RF signal to track movement of scatterers 44 in the fluid medium 34. In any event, it will be appreciated that the availability of two algorithms, the FFT method for the spectral analysis and the Burg autoregressive method algorithm for the peak frequency respectively flow velocity would be ideal.

The received reflection signal is conveniently digitised for processing by the module 94. Also, it will be appreciated that the module 94 is conveniently configured to apply algorithms for detecting the Doppler shift frequency or time delay and these may be divided into spectral (FFT) and time domain algorithms.

The electronics and signal processing elements 80 conveniently have direct access to 'raw data' from the transducers 40 and 42 to allow for increased control of signal quality and gain amplification levels, detection of signal artifacts as well as correction of aliasing phenomena.

In any event, as mentioned above, the module 94 is configured to determine velocity profile of the fluid flow 34 in the time or frequency domain, optionally selectable by a user of the system 10. A complex Doppler signal is given by:

$$f(t)=I(t)+iQ(t), \quad \text{(Equation 1)}$$

where I(t) and Q(t) are the in-phase and co-phase signal components, respectively. The Fourier transform of the Doppler Signal is calculated as follows:

$$\hat{f}(\omega)=\int_{-\infty}^{\infty} f(t)e^{-i\omega t}dt, \quad \text{(Equation 2)}$$

and the power spectrum $S(\omega)$ is given by:

$$S(\omega)=\widehat{f^*}(\omega)\hat{f}(\omega). \quad \text{(Equation 3)}$$

The module 94 implementing the frequency domain algorithm is configured to implement the Burg algorithm, a parametric spectral estimation method, which determines an estimate of the power spectrum of the complex echo signal (reflection signal) constructed from the in-phase (I) and co-phase (Q) echo data (raw data). The Doppler frequency corresponding to the maximum power point or peak is selected by the module 94 for velocity estimation and is calculated by:

$$v = \frac{cf_d}{2f_c\cos\theta}. \quad \text{(Equation 4)}$$

The time domain algorithm applied by the module 94 determines the Doppler frequency shift in terms of the measured I and Q components of the complex experimental Doppler signal (for example, from Barber, W. D., Eberhard, J. W. & Karr, S. G. 1985. A New Time Domain Technique for Velocity Measurements Using Doppler Ultrasound. *IEEE Transactions on Biomedical Engineering*, BME-32(3): 213-229):

$$f_d = \frac{1}{2\pi PRF}\tan^{-1}\left(\frac{\sum_{i=1}^{M}(Q_i*I_{i-1} - Q_{i-1}*I_i)}{\sum_{i=1}^{M}(I_{i-1}*I_i + Q_{i-1}*Q_i)}\right). \quad \text{(Equation 5)}$$

This approach is based on the expression for the instantaneous rate of change of phase which separates rapidly varying from slowly varying terms. This technique solely relies on signal processing in the time domain, which advantageously makes it significantly simpler to implement relative to the classic FFT approach.

It follows by using several velocity estimation algorithms (time domain and frequency domain) at the same time, the module 94 advantageously provides enhanced accuracy and quality of measured velocity profiles.

The velocity profiles as determined by the velocity estimating module 94 are generally not known with sufficient accuracy as a result of the effect of the finite sample volume characteristics and propagating through solid boundaries or wall material layers. It will be understood that this could be the delay line material, front plate, or wall of a pipe.

Figure 12:
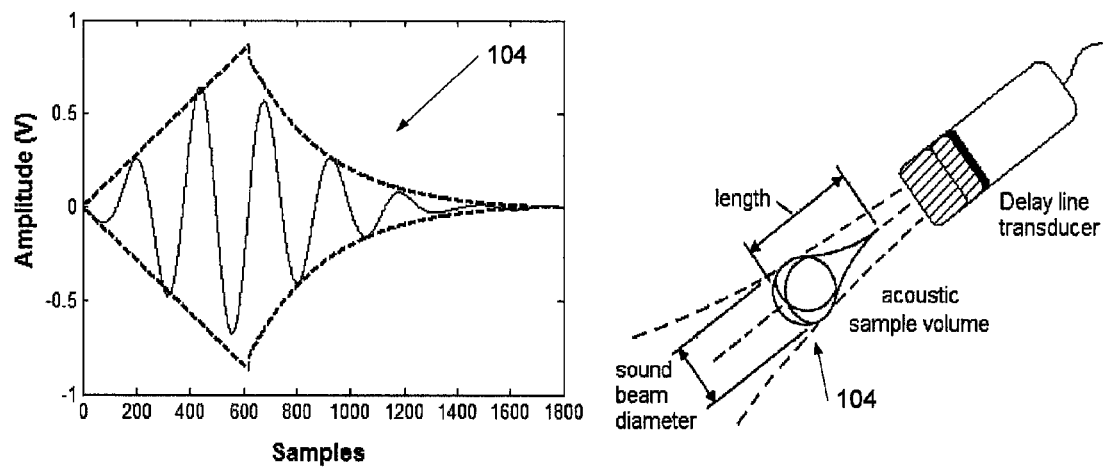
FIG. 12 shows a drawing illustrating a delay line transducer sample volume in accordance with an example embodiment.

Referring to FIG. 12, the sample volume 104 has a teardrop or drop-shaped geometry. For a short driving pulse the ultrasonic wave intensity increases exponentially until the end of the electrical pulse followed by a gradual decay due to the transducer 40 ringing phase (exponential decay of stored energy). Sound field characteristics of the sample volume 104 are determined by the ultrasonic transducer 40 focal properties, the sound scatterers 44 in the flow medium and the sensitivity of the receiver circuitry. The acoustic signal transmitted by the transducer 40 is an acoustic burst and is a three-dimensional region of sound intensity and any flow particles passing this region produce Doppler signals which are detected by the second transducer 42.

Since multiple scatterers 44 flowing at different velocities are present in the practical environment the received signal is a spectrum of frequencies containing the Doppler shifts of all moving particles 44. The result of this spectral broadening is that, in small tubes/pipes where the velocity gradients are high, the velocity profiles are considerably distorted. This distortion is caused by the averaging which takes place over the sample volume 104. It is assumed that the measured velocity is proportional to the average of the velocities within the sample volume 104 weighted by the associated intensity distribution of the measuring volume. Mathematically, the measured velocity profile can be expressed as a three-dimensional convolution of the real velocity profile with the sample volume intensity function (e.g. from Jorgensen, J. E., Campau, D. N. & Baker, D. W. 1973. Physical characteristics and mathematical modelling of the pulsed ultrasonic flowmeter. Medical and Biological Engineering, 11(4): 404-421):

$$v_m(r) = \frac{\int_0^r \int_{z_1}^{z_2} \int_{y_1}^{y_2} v_t(x, y, z) i(r-x, y, z) dx dy dz}{\int_{z_1}^{z_2} \int_{y_1}^{y_2} \int_{x_1}^{x_2} i(x, y, z) dx dy dz},$$ (Equation 6)

where r is the range variable (distance along path of ultrasonic propagation).

The convolution procedure can be dramatically simplified by assuming that the sample volume 104 has only one dimension, its length and that it is characterised by the acoustic intensity along the ultrasonic beam axis 43. Since the length of the sample volume is both its largest dimension and is coincident with the direction of convolution and since the intensity is the highest at the beam centre, these assumptions prove to be reasonable (Jorgensen, J. E. & Garbini, J. L 1974. An Analytical Procedure of Calibration for the Pulsed Ultrasonic Doppler Flow meter. *Journal of Fluids Engineering*, 96: 158-167). Equation 6 then reduces to a one-dimensional convolution:

$$v_m(r) = \int_0^r v_t(x) i(r-x) dx.$$ (Equation 7)

Another way of calculating the measured profile is by applying the time convolution theorem, which states that the Fourier transform of the convolution (*) of two functions is equal to the product of the two Fourier transforms ($\Im(f_1(t)*f_2(t)) = F_1(w)F_2(w)$ where $\Im$ is the Fourier transform operator and $F_1(w)$ and $F_2(w)$ are the Fourier transforms of $f_1(t)$ and $f_2(t)$ respectively. After a few more transformations the real or 'true' velocity profile can be calculated using a deconvolution process:

$$v_t(r) = \mathcal{F}^{-1}\left(\frac{V_m(k)}{I(k)}\right),$$ (Equation 8)

where k has the inverse dimension of the spatial coordinate (Flaud, P., Bensalah, A. & Peronneau, P. 1997. Deconvolution process in measurement of arterial velocity profiles via an ultrasonic pulsed Doppler velocimeter for evaluation of the wall shear rate. Ultrasound in Medicine & Biology, 23(3): 425-436).

In the light of the above, the processor 94 advantageously comprises a deconvolution module 100 configured to apply a deconvolution algorithm to the velocity profile determined by the velocity estimating module 98 to determine a deconvolved or true velocity profile of the fluid flow 34 in the pipe and thus the erroneous velocity data caused by the finite size of the sampling volume characteristics of the previously determined velocity profile is corrected for.

Figure 14:
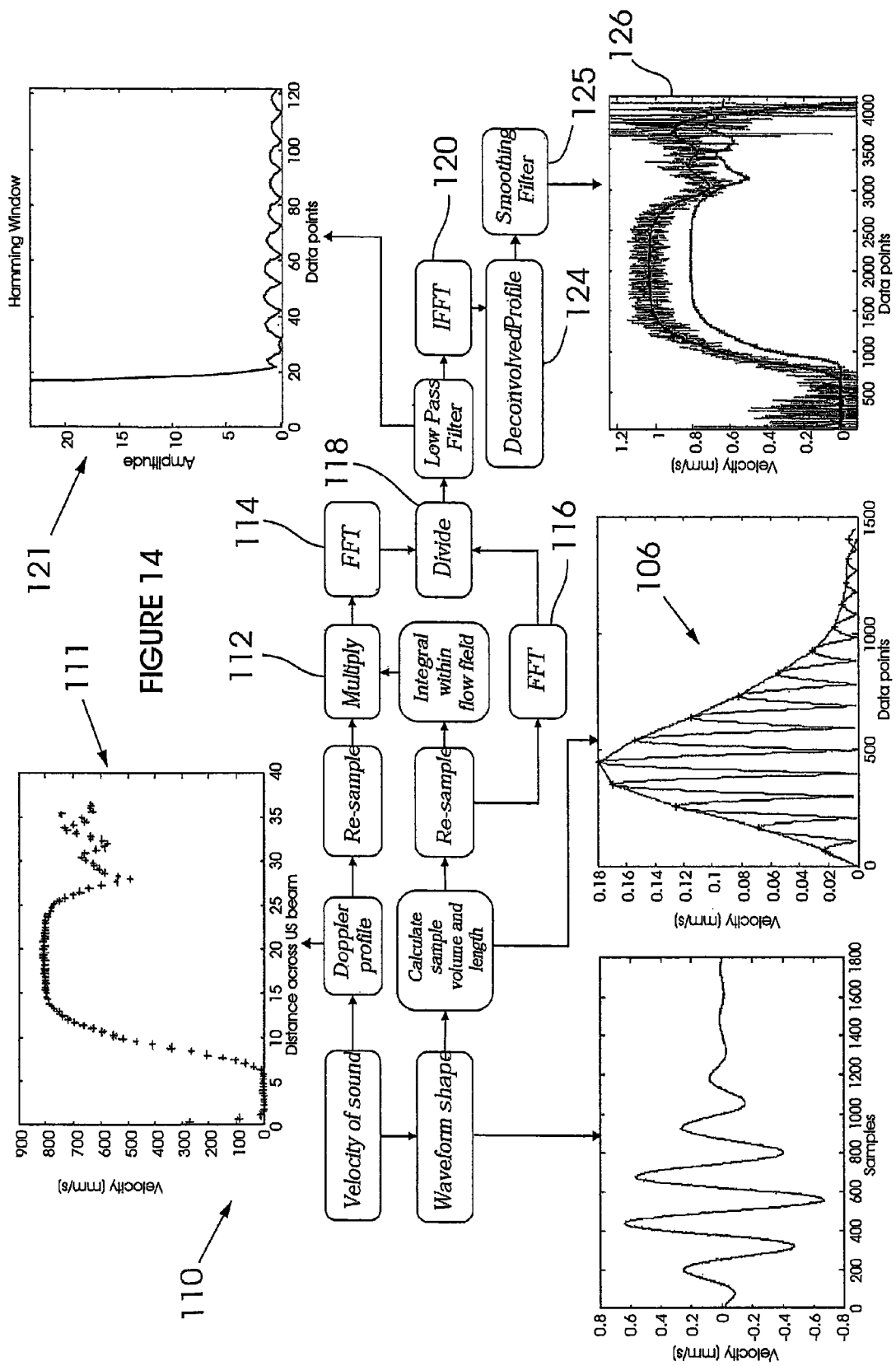
FIG. 14 shows a conceptual process flow diagram illustrating the steps of the deconvolution algorithm in accordance with an example embodiment.

Reference is now made also to FIG. 14 where a conceptual process flow diagram of the deconvolution algorithm applied by the module 100 is indicated by reference numeral 110. Firstly, the module 100 is configured to receive and store in the memory 96, a velocity profile as determined by the velocity estimating module 98, followed by the velocity of sound parameter and waveform shape.

The velocity of sound parameter is advantageously determined by the velocity of sound calculation module 103. The velocity of sound parameter is the speed of the sound wave transmitted in the fluid medium (measured using the two opposite mounted transducers 40, 42). The velocity of sound value is used to determine the length of the sample volume as velocity=distance/time. The sample volume (or waveform) measured on, for example, an oscilloscope as a function of time and thus there is a need to convert the time axis over which the sample volume is measured to distance (because the velocity profile is a function of radial distance), for ease of subsequent calculation.

The waveform shape on the other hand is the actual measured signal, i.e. a sinusoidal signal. The sample window gets determined from the waveform shape by determining the envelope of the waveform shape and then normalising the sample window.

Figure 13:
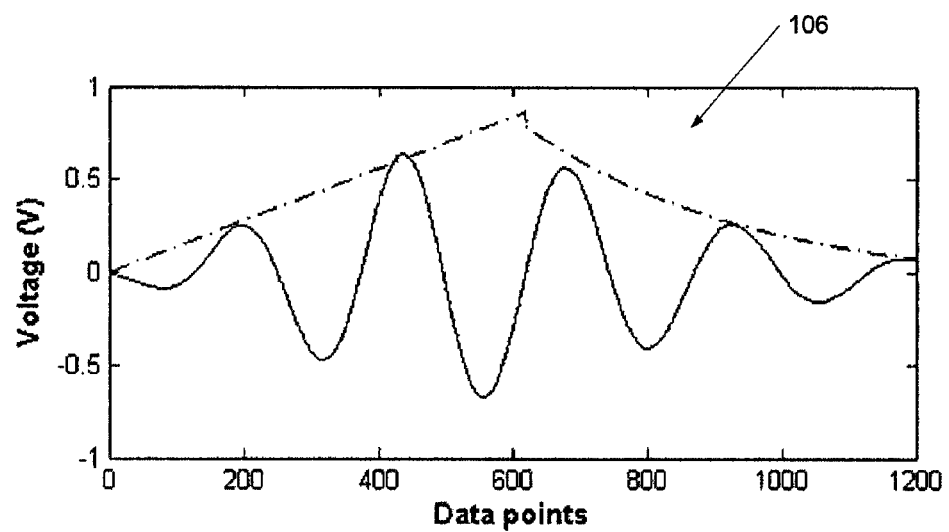
FIG. 13 shows a drawing illustrating a transducer response in accordance with an example embodiment.

Reference is now made to FIG. 13, which shows a sampling window 106 (envelope of waveform shape) constructed from a measured waveform (sampling volume) used by the module 100.

It will be appreciated that the 'sample window' is not the 'sample volume' (3D shape), but the envelope of the 2D waveform measurement (shown in FIG. 13). The area of the sample window is determined (by integration) as the window enters and exits the pipe wall boundaries, thus the area of the window upon entry and exit will not be constant as not the entire window is situated inside the flow area. In other words, the waveform shape is simply the envelope of the ultrasound signal transmitted by the one transducer (which is received by the opposite transducer or vice versa). The 'sample volume' is a term used to describe the physical pressure wave pulse that is transmitted into the fluid medium, i.e. it is actually the envelope of the measured waveform shape rotated around its horizontal axis (see FIG. 13) to form a 3D 'tear drop' shape (see FIG. 12).

As an aside, it will be appreciated that the window 106 is described by the envelope of the exponential rise and decay of the intensities which lie on the sample volume axis. The system determines the sample window used for deconvolution, i.e. the actual length of the window in meters as well as the normalised envelope of the measured waveform shape (which is measured in voltage vs. time using for example an oscilloscope or other means).

The shape and length of the sampling window 106 significantly controls the outcome of the deconvolution procedure implemented by the deconvolution module 100, i.e. any errors will result in a deconvolved profile which contains large amount of noise and distortion. The magnitude of the deconvolved velocity profile is also particularly sensitive to the overall shape and area of the sampling window 106. Therefore the described technique of continuously monitoring the sampling window 106 is especially important as the shape and length of the window varies according to the velocity of sound in the medium, temperature, density as well as attenuating properties of a particular test fluid.

For clarity regarding the continuous sampling window 106, it will be noted that one transducer 40 transmits a wave in the fluid medium and the opposite transducer 42 receives the waveform which is digitally recorded for processing. This can be continuously monitored in both directions (transducer 42 transmits and transducer 40 receives).

In any event, the electronic elements 80, or the processor 94, are configured to normalise the waveform or sampling window 106 before the module 100 implements the deconvolution algorithm in order to correct erroneous velocity data caused by the convolution of the finite sampling window and true flow profile in the pipe or other geometry.

In particular, the normalised sampling window is determined from the measured waveform shape by detecting an envelope of the measured waveform shape (the sample window) and dividing all sample points on the sample window by the sample window's maximum magnitude value.

A length of sample window is then determined by multiplying a time axis with the measured velocity of sound parameter.

The recorded velocity profile and determined sample window is then re-sampled so that the number of samples correspond to correct distances of the sample window and radial distance of the stored velocity profile.

In any event, the module 100 is configured to multiply, at block 112, the measured velocity profile or Doppler profile (illustrated as 111) by the integral of the sampling window 106 within the flow field, to account for the normalising function in the primary model assumption, thereby to obtain a first multiplication product. This is not a constant value, because upon entry and exit only part of the sampling window 106 is contained within the flow field. For brevity, it will be appreciated that the "flow field" is the flow across the pipe diameter, as the sample window travels from the transducer across the pipe diameter. The sample window will initially not be entirely contained within the flow region, the same goes for when the window exits the opposite side of the flow region, the window travels from the transducer surface across the pipe diameter and exits the same.

The module 100 is then configured to apply, at block 114, a Fast Fourier Transform (FFT) algorithm, particularly a Discrete Fourier Transform (DFT), to the first multiplication product to obtain a first FFT result. The module 100 is also arranged to apply a FFT algorithm, at block 116, to the sample window/sample volume 106 to obtain a second FFT result.

The module 100 then conveniently is configured to divide, at block 118, the first FFT result by the second FFT result to obtain a first division quotient.

This may optionally be repeated as described above and as illustrated as per the re-sampling mentioned above.

The module 100 is also configured to apply, at block 120, a low pass filter (illustrated as 121) to the first division quotient to obtain a low pass filtered first division quotient. In this way, unwanted noise is removed with a digital low pass filter before the final deconvolved profile is used for detailed flow analysis. It will be noted that an option the unprocessed profile or data may also be used for further calculations.

The module 100 is also configured to apply, at block 122, an inverse FFT (IFFT) to the low pass filtered first division quotient to obtain the deconvolved velocity profile, at block 124. A smoothing filter is applied at block 125 in order to remove unwanted noise and enhance the quality of the data, with the resultant deconvolved velocity profile being illustrated at block 126.

The module 100 is also conveniently configured to calculate, at block 108, the sample volume 106 as hereinbefore described.

Advantageously, the deconvolution steps carried out by the module 100 requires only information of the measured profile and sampling window length and shape. No prior knowledge of the nature of the true velocity profile is required.

With the determined deconvolved velocity profiles and determined velocity profiles as well as measurements from the sensor, the system 10 may conveniently determine characteristics of the fluid flow 34 in a pipe. To this end, the system 10, typically the processor 94, comprises a fluid characterisation module 102 configured at least to determine fluid characteristics, rheological parameters, etc. of the fluid flow 34 by using inputs received from the sensors 60, and 64 as well as the determined velocity profiles, and deconvolved velocity profiles.

The fluid characterisation module 102 may be configured to determine shear rate distribution substantially simultaneously from a measurement of the pressure difference from the pressure sensor 60. In particular, the fluid characterisation module 102 may be configured to use the pressure difference from the pressure sensor 60 in combination with the deconvolved velocity profile to determine shear viscosities and rheological model parameters.

The fluid characterisation module 102 may be configured to determine shear viscosities and rheological model parameters by non-linear fitting of determined velocity profiles and measured pressure differences to rheological models. Alternatively, and preferably, the fluid characterisation module 102 may be configured to use a non-model approach, known as the gradient method, to determine shear rate distribution from a velocity gradient of the determined velocity profiles and optionally a shear stress at a wall of the pipe 46, e.g., via cubic-spline interpolation or polynomial model-fitting followed by numerical derivation.

In any event, it will be appreciated that the module 102 may be configured to determine the shear stress at the wall (and hence also the distribution) from the pressure drop over a fixed distance, knowing also the diameter of the pipe.

It will be appreciated that the shear rate distribution on the other hand may be determined by the module 102 in two ways; 1) mathematical models describing the velocity distribution in a pipe as function of radius are well-known and can be derived (Power-law, Bingham, Herschel-Bulkley etc.). The deconvolved velocity profiles determined above can thus be fitted to such model.

Alternatively, 2) any other mathematical equation capable of describing a somewhat parabolic shape (polynomial, power, cubic spline, etc.) may be used by the module 102 for describing the deconvolved profile. However, a major problem with e.g. high-order polynomials and splines is that they are prone to fluctuations, which results in inaccurate description of the deconvolved profiles if the data contains noise (which is often the case). The module 102 therefore advantageously uses another procedure involving e.g. a smoothing filter that eliminates mentioned fluctuations and results in a true mathematical representation of the deconvolved profiles.

The first derivative of the velocity distribution is the shear rate and it can thus be obtained from either the model-fitting procedure or directly from the velocity profile using a non-model approach e.g. cubic-spline interpolation or polynomial model-fitting followed by numerical derivation. It should also be noted that the model-fitting procedure can be omitted and the shear rate can thus be obtained by direct numerical derivation.

Shear viscosities are obtained from the quotient of the shear stress over the shear rate distribution.

Rheological model parameters may be obtained by non-linear fitting of determined velocity profiles and measured pressure differences to rheological models.

The system 10 may comprise, or the fluid characterisation module 102 is conveniently configured to interact with, an input/output user interface 87 to provide determined and/or measured information to a user. The user interface 87 may comprise a laptop, a PC (Personal Computer), or suitable computing device to receive information from the system 10 and to provide the same to the user, e.g., by way of a display device (e.g., an LCD (Liquid Crystal Display), LED (Light Emitting Diode), CRT (Cathode Ray Tube) screen, or the like). The user input may comprise a keyboard, mouse, touchscreen, or the like to receive inputs from the user. Information may typically be provided to the user by way of a suitable graphical user interface (GUI) or HMI (Human Machine Interface) displayable by the user interface 87.

It will be appreciated that the module 102 may be configured to display the determined velocity profiles, deconvolved velocity profiles, pressure measurements, and temperature measurements in a visual format to the user by way of the user interface 87. In certain example embodiments, the module 102 is configured to generate graphs indicative of the above for display to the user. The module 102 may also generate models for visualisation of the characteristics of the fluids flowing in a pipe of interest.

It will be appreciated that the system 10, particularly the electronics and signal processing elements 80, may comprise means for passing a section of received reflection signal in an adjustable time window relative to the transmitted waveform (pulse), thereby providing a gated received signal that may be filtered, demodulated to produce a frequency shifted sample signal and to perform operations to determine the frequency shift, time- or phase delay associated with a region of the fluid flow.

The processor 94 may be configured to adjust the time window to determine local velocity in each sampling volume and complete instantaneous velocity distribution as a function of time or distance along each measuring axis, line.

The processor 94 may also be configured to determine one or more shear-dependent viscosities and model parameters of the fluid flow and to calculate shear rate and shear stress distribution.

It will be appreciated that the system as described herein is able to determine the velocity profile and thus also rheological parameters in fully developed, steady laminar flow but also in intermediate and turbulent flows where the Reynolds number is greater than 2300.

Figure 15:
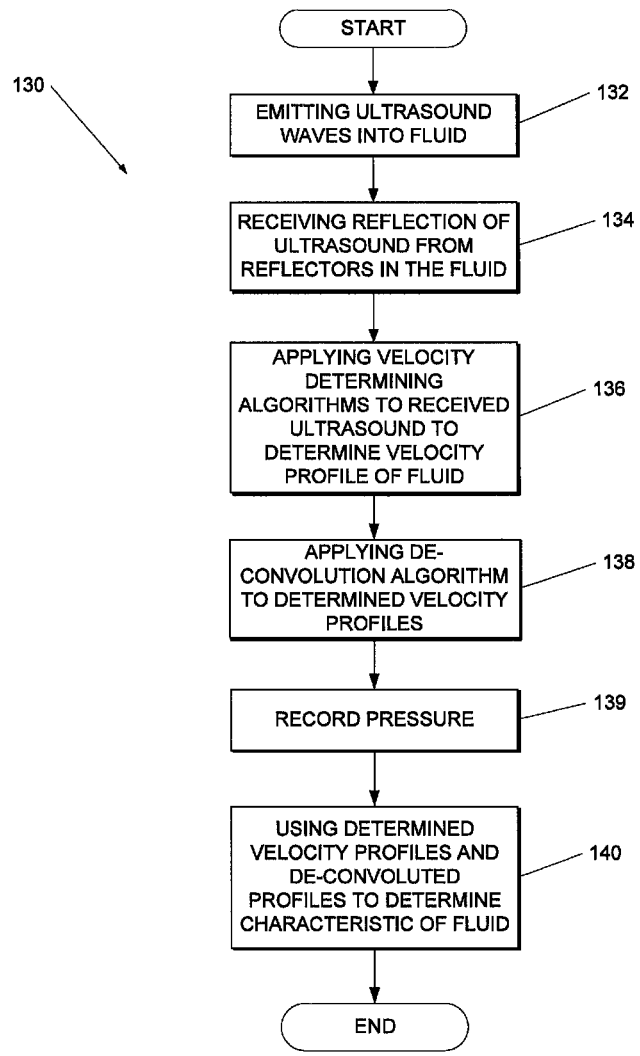
FIG. 15 shows a high level flow diagram of a method in accordance with an example embodiment.
Figure 16:
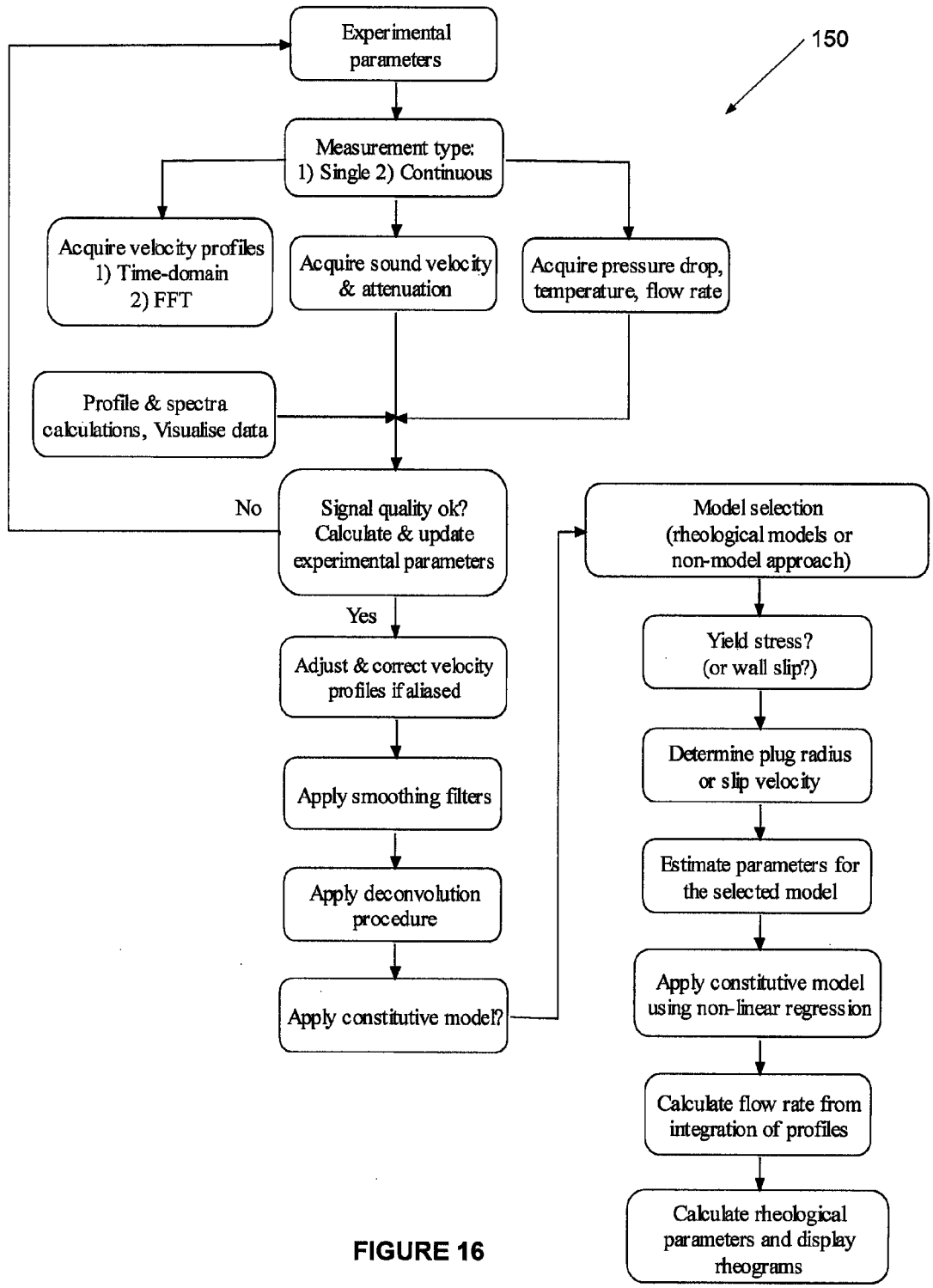
FIG. 16 shows another high level flow diagram of a method in accordance with an example embodiment.

Example embodiments will now be further described in use with reference to FIGS. 15 and 16. The example methods shown in FIGS. 15 and 16 are described with reference to FIGS. 1 to 14, although it is to be appreciated that the example methods may be applicable to other systems (not illustrated) as well.

Reference is made firstly to FIG. 15 of the drawings where a flow diagram of a method for characterising fluids flowing in a pipe is generally indicated by reference numeral 130. The method 130 is typically carried out in an industrial processing plant comprising networks of pipes containing fluids (e.g., liquids, emulsions, suspensions, sludge, or the like) where it is desirous to know and visualise the fluid characteristics of the fluids in the pipes.

The method 130 comprises emitting, at block 132 by way of the first delay line transducer 40, a high frequency signal into the fluid flow 34.

The method 130 then comprises receiving, at block 134 by way of the second delay line transducer 42, the reflection signals along the measurement axis 43 in the fluid flow 34.

The method 130 comprises applying, at block 136 by way of the velocity estimating module 98, one or more velocity determining algorithms to the received reflection/signals to determine a velocity profile of fluid flow 34 in the pipe under investigation/analysis, in a fashion as hereinbefore described.

The method 130 then advantageously comprises applying, at block 138 by way of the module 100, a deconvolution algorithm to the determined velocity profile to determine a deconvolved velocity profile of the fluid flow in the pipe substantially in the manner as previously described.

The method 130 comprises determining and recording, at block 139, pressure as hereinbefore mentioned.

The method 130 then comprises determining, at block 140 by way of the fluid characterisation module 102, fluid flow characteristics of the fluid flowing in the means defining the fluid flow path by using the determined velocity profiles and/or the deconvolved velocity profile as described above.

Reference is now made to FIG. 16 of the drawings where another flow diagram of a method in accordance with an example embodiment is generally indicated by reference numeral 150.

The method 150 is an automated method and is typically performed in real-time. Experimental parameters (RF echo data, sound velocity, pressure, temperature, flow rate, pulse waveforms, attenuation) are recorded using the digital data acquisition device 92 with interface to a PC. As described earlier, the present invention is capable of estimating velocity using time and frequency domain algorithms. Raw RF echo data obtained from each pulse is recorded, which is used in velocity estimation algorithms, but also for visualisation and monitoring of the spectral content of the Doppler shift frequencies for enhanced quality control of velocity measurements. Errors caused by aliasing can also be corrected for by applying error correction software (e.g., by way of the processor 94) to the measured data.

This is especially important for open channel flow applications (discussed below), where the UVP technique needs to measure across large flow depths and at high flow velocities. The UVP technique suffers from a double limitation in this regard since higher flow velocities in open channels result in higher flow depths or larger penetration depths at the same time.

After data acquisition, the quality of the measured data can be enhanced by applying various smoothing filters (such as Singular Value Decomposition, Finite Impulse Response, Infinite Impulse Response and Moving Average filters), which can be selected by the user via the present invention's GUI. Commercial UVP instruments usually employ one simple low pass filter, which is typically incorporated into hardware or the instrument's DSP. Depending on the application, this could result in noisy and bad quality data, which can result in significant errors in profile measurements and ultimately the rheological parameters determined using the UVP+PD methodology. Access to different filters via the GUI allows users to maximise the quality of recorded data by selecting a custom filter that works best for a particular application.

After velocity profiles are calculated and visualised by the software a deconvolution procedure is applied in order to correct near wall velocity data and gradients for accurate calculation of flow rates (by integration) as well as rheological parameters. Once the accuracy and quality of the experimental parameters (pressure, RF echo data, velocity profiles) have been established to be at an acceptable level, the rheological parameters, volumetric flow rate and other parameters such as attenuation properties and solids concentration are calculated by the module 102 in a conventional manner. The solids concentration is monitored for example by continuously monitoring the velocity of sound parameter in the fluid medium of interest. Attenuation on the other hand is monitored by recording the waveform shape (voltage vs. time) and monitoring the magnitude of the energy (or voltage) of the waveform shape. The user has access to different model fitting techniques and rheological models (such as the power-law, Bingham, Herschel-Bulkley, Sisko, Casson, Cross, Ellis, Carreau or similar models).

Shear viscosities and rheological model parameters can be obtained in two ways: either from a non-linear fit of the measured velocity profiles and pressure drop data to suitable rheological models, as described above, or directly from the velocity profile and pressure drop using a non-model approach. The present invention primarily makes use of, by way of the module 102, the latter approach, which has the advantage that it requires no "a priori" knowledge of the flow behaviour of the fluid systems. It also has the disadvantage of requiring high spatial resolution and high data quality, which can be obtained using delay line transducers 40, 42 plus deconvolution.

In one embodiment, the shear rate distribution is then determined directly from the velocity gradient of the acquired velocity profiles, e.g. by direct numerical derivation or via cubic-spline interpolation or polynomial model-fitting followed by numerical derivation. In the preferred embodiment, a smoothing filter is applied to the measured and deconvolved velocity profile to determine the smoothed value for each point prior to determining the shear rate distribution, shear viscosities and/or rheological parameters. The main advantage of this approach is that it preserves features of the distribution such as relative maxima, minima and width, which are usually 'flattened' by other adjacent averaging techniques (like moving averages, for example).

The main steps of the above-mentioned non-model approach can be summarised as follows:
1. Record the velocity profile and velocity of sound
2. Apply appropriate smoothing filter to enhance quality of velocity profile data
3. Apply a deconvolution procedure if necessary
4. Conduct a cubic-spline interpolation or polynomial model-fitting to the velocity profile (this is an optional step)
5. Apply an advanced Savitzky-Golay smoothing filter to the determined velocity profiles and/or deconvolved velocity profiles prior to obtaining the velocity gradient (shear rate distribution)
6. Apply numerical derivation to the processed velocity profile
7. Calculate the maximum shear rate and shear rate distribution The non-model fitting technique increases the overall accuracy of in-line rheological parameters determined using the UVP+PD methodology.

These comments also apply substantially to the UVP+FD methodology described below.

Figure 17:
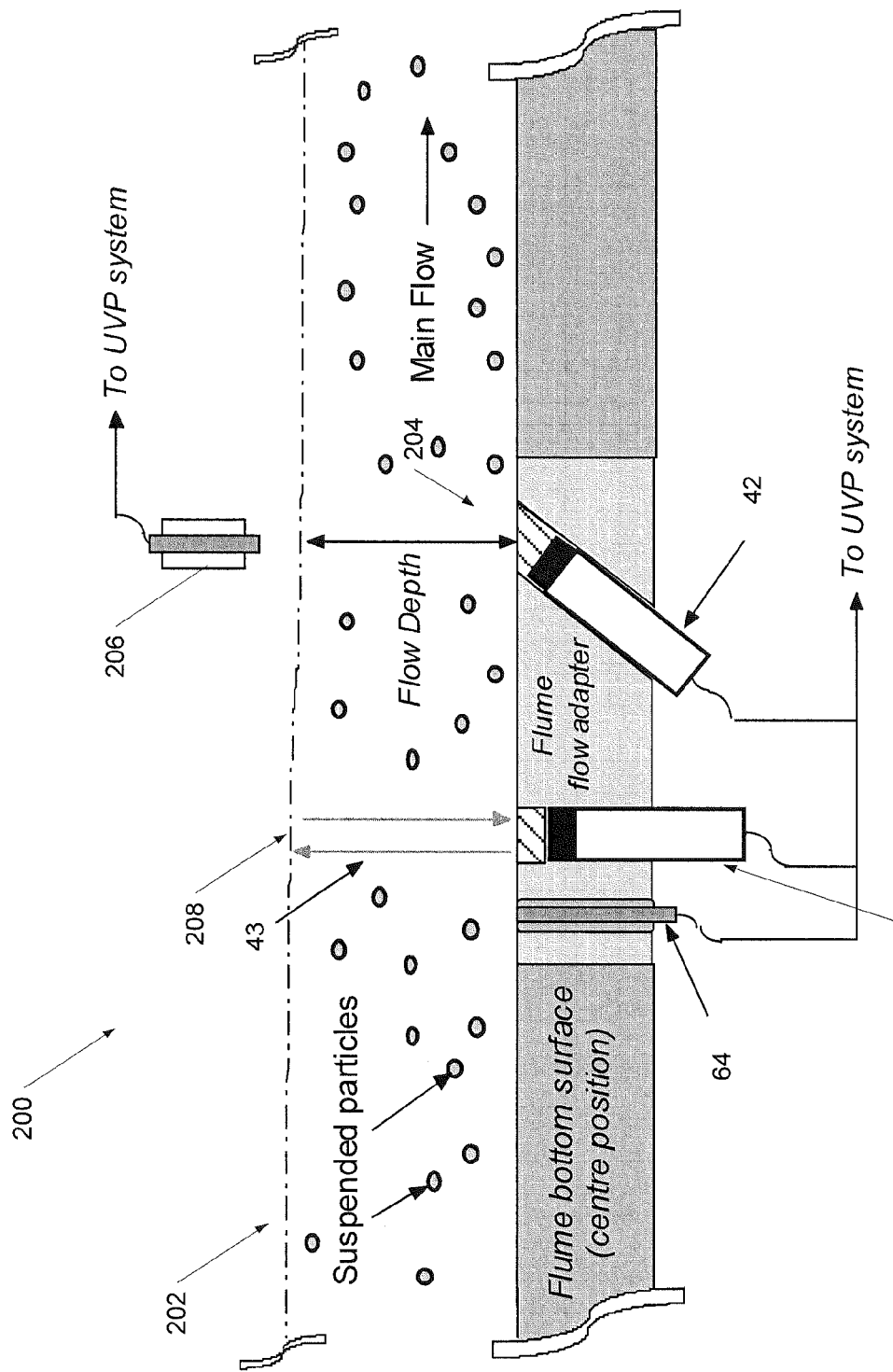
FIG. 17 shows a schematic, part-section, illustration of another configuration of the fluid visualization and characterisation system, particularly a measuring section thereof, in accordance with an example embodiment.

Reference is now made to FIG. 17 where another example embodiment or configuration of a system, particularly the measuring section thereof required for in-line rheology in non-Newtonian open channel flow, is generally indicated by reference numeral 200.

The measurement section 200 is similar to the measurement section 30 and similar parts will be referenced by the same reference numerals.

For open channel flow in a channel 202, it is possible just as for pipe flow (UVP+PD methodology described above) to establish the rheological parameters by fitting theoretical models to experimental data. Only one velocity profile measurement at the centre of the flume or open channel and the corresponding flow depth/height in laminar flow is required. This method also uses the delay line transducer technology as hereinbefore described as well as the same electronics and signal processing elements as hereinbefore described.

First and second transducers 40, 42 are installed along with the temperature sensor 64 at a bottom centre surface 204 of a flume or open channel 202. A flow depth measurement sensor 206 is installed above the transducers 40, 42, which can measure the distance between the sensor and fluid level thereby to measure the flow depth of the flume 202. It will be appreciated that the total distance between the distance sensor's 206 surface is calibrated and the fluid level is then determined by simply subtracting the total calibrated distance with the measured distance.

The sensor 206 is typically a conventional ultrasonic or infrared distance sensor which is configured to operate accurately in air. It will be understood that the flow depth needs to be measured very accurately as this parameter can significantly influence rheological parameters determined by model fitting onto experimental data. The first transducer 40 is mounted transverse to, for example, at 90 degrees to the main fluid flow 34 to measure the velocity of sound by recording the time-of-flight of an ultrasonic pulse which travels along the measurement axis 43 from the ultrasonic transducer's surface 40 to the fluid liquid/air interface 208 and back. The liquid/air interface 208 has a large acoustic impedance which provides good echo towards the ultrasonic transducer 40. However, this configuration has the disadvantage of the ultrasonic wave that has to travel twice the fluid flow depth distance, which in attenuating fluids could cause problems. In this regard, it will be appreciated that the velocity of sound measurement system and method in pipe flow (UVP+PD described above) does not suffer from this drawback as two transducers 40 and 42 are mounted at opposite sides of one another along a measurement axis 45, where one transducer transmits and the other receives. It should also be noted that the previous mentioned disadvantage can be eliminated by using one transducer in emitting and receiving mode for velocity of sound measurements.

It will be appreciated that the transducer 40 operates in transmitting/emitting mode as well as receiving mode to emit ultrasound signals into the fluid flow 34 and receive reflection signals accordingly.

Optionally another transducer 42, also configured to operate in transmitting and receiving mode, may be mounted at an angle for measurement of instantaneous velocity profiles across the flume flow section. Velocity data near the liquid/air interface of the measurement axis are distorted due to multiple reflections from the air interface, which is inherent in any UVP instrument or application. In pipe flow this does not matter as only half of the profile across the measurement line is required due to the symmetrical geometry of a straight pipe. The flow behaviour in a flume 202 is asymmetrical across the flow depth or measurement axis 47 and thus velocity data near the liquid/air interface need to be corrected for by applying signal processing techniques such as interpolation.

Figure 18:
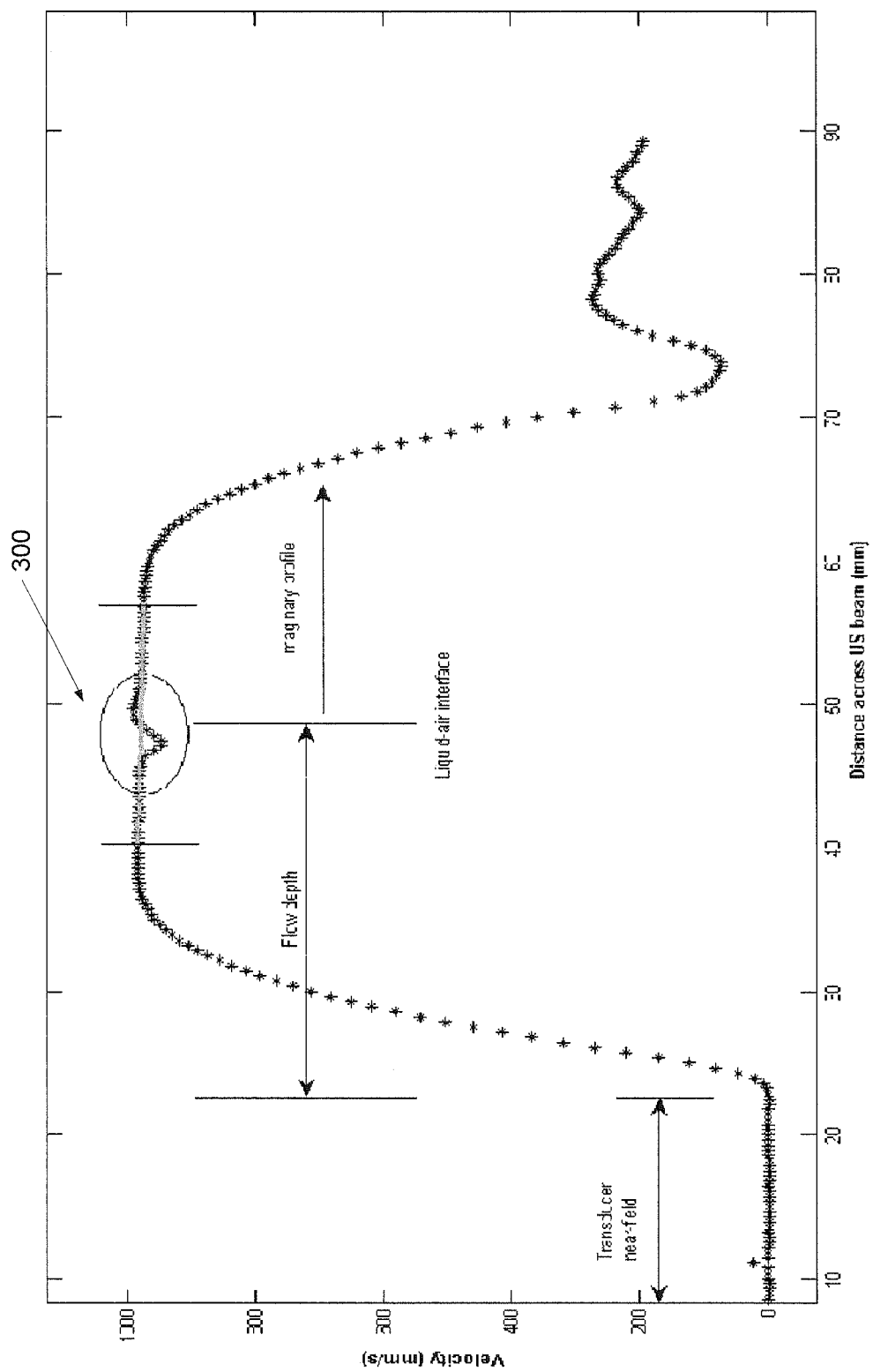
FIG. 18 shows an illustration of a flume profile in accordance with an example embodiment.

Referring to FIG. 18, it will be noted that the correction referred to is to correct an increase and decrease of velocity magnitudes at the region of liquid/air interface 300. The data associated with this region 300 is discarded and these 'missing' points at this region is corrected for by interpolating across the measured profile before the liquid-air interface as well as an imaginary profile plotted beyond the liquid-air interface. The imaginary profile that is recorded occurs due to multiple ultrasonic reflections from the air interface (high acoustic impedance). This effect is known as reflected wave effect.

In any event, the measurements obtained by the measuring section 200 may conveniently be used by the electronics and signal processing elements 80 in a similar fashion as hereinbefore described, though without application of the UVP+PD elements as hereinbefore described.

The present invention provides a convenient, stand-alone UVP+PD system capable of in-line fluid visualisation and rheological characterisation. The present invention could be used with a plurality of transducer pairs thereby enabling measurements along several measuring lines, which allows monitoring of flow symmetry but also in combination with the deconvolution procedure, which corrects distorted velocity data caused by the finite sample or measuring volume crossing material boundary layers. The transducers are installed flush with the inner diameter of the pipe making this setup ideal for industrial process control and monitoring. Having the functionality to determine velocity profiles in pipe flow with high accuracy close to pipe walls is also advantageous as this is critical for accurate fluid characterisation.

Fluid properties such as speed of sound and ultrasound attenuation in the medium can also be monitored in-line by using two transducers installed in opposite directions of one another. Furthermore, the present invention is advantageously able to estimate velocity profiles using several different algorithms (time and frequency domain), various smoothing and wall filters and advanced model fitting techniques for enhanced quality and accuracy of measurements such as flow behaviour, rheological parameters, velocity of sound, SFC, fluid attenuation properties as well as solid concentration gradients.

The delay line transducers as hereinbefore described provide acoustic pulses that can penetrate across large pipe diameters commonly found in industrial applications, and at the same time preserve the shape of the beam/pulse (measuring volume). They further allow, for the first time, accurate velocity measurements directly from the transducer front and within the near-wall layer.

In addition, the present invention provides a system and method that allows real-time measurements of radial velocity profiles and rheological properties, such as yield stress directly in-line. It has advantages over commercially available process rheometers and off-line instruments in being non-invasive, applicable to opaque and concentrated suspensions, having small sensor dimensions and at relatively low cost.

The present invention also provides a system and method for real-time data processing and is able to display instantaneous results, which can be presented in different formats or specifications e.g. viscosity vs. shear rate, shear stress vs. shear rate, log-log scales etc. Furthermore, current commercial UVP instruments are only capable of estimating velocities across the ultrasonic beam axis using one algorithm, usually integrated in the Digital Signal Processor (DSP). Existing systems also employ simple and standard filters for noise reduction caused by low signal-to-noise ratios or other artifacts during measurements, which result in noisy data and erroneous velocity estimations. The present invention and software is able to switch between different velocity estimation algorithms (time-domain and frequency domain) and different filters, optionally selectable by the user, for improving data quality as well as overall accuracy.

What is claimed is:

1. A liquid visualization and characterisation system comprising:
    a measuring section comprising a housing having a pipe which has an outer wall, the pipe defining a liquid flow path for flow of a liquid having particle or bubble reflectors dispersed therewithin, the measuring section including:
        at least one transducer having a front end disposed exteriorly of the pipe and configured to convert an electric signal into an ultrasonic signal and to transmit the ultrasonic signal into the liquid flow in the pipe and wherein the transducer is arranged to be used in conjunction with a delay line element which is provided at the front end of the transducer and wherein the delay line element is configured to enhance acoustic characteristics of the ultrasonic signal generated by the at least one transducer, the delay line element being disposed in contact with the outer wall of said pipe in a non-invasive measurement configuration, and wherein, when the ultrasonic signal is transmitted into the liquid flow in the pipe, reflectors in the liquid flow reflect the signal to form backscattered ultrasonic signals; and
        at least one receiver configured to receive the backscattered ultrasonic signals from reflectors in the liquid flow;
    a memory for storing data; and
    a processor operatively connected to the memory, the processor comprising:
        a velocity estimating module configured to apply one or more velocity estimation algorithms to the received reflections of the ultrasonic signal, or data indicative thereof, to determine an instantaneous velocity profile of liquid flow in the pipe defining the liquid flow path, wherein the instantaneous velocity profile is a velocity distribution of liquid flow as a function of distance along a measuring axis of the pipe;
        a deconvolution module configured to apply a deconvolution algorithm at least to the determined instantaneous velocity profile to determine a true instantaneous velocity profile of the liquid flow in the pipe defining the liquid flow path;
        a fluid visualization and characterisation module configured to determine instantaneous rheological properties of the liquid flow in the pipe defining the liquid flow path by using one or both of the determined instantaneous velocity profile and the true instantaneous velocity profile,
    wherein the delay line element has an acoustic wedge and acoustic couplant, and wherein the delay line element is configured so that a focal point of the ultrasonic signal transmitted by the transducer is located at a liquid-wall interface of the measuring section where the ultrasonic signal enters the liquid flow path, thereby ensuring that no velocity measurements are made within a near-field distance of the transducer.

2. The system of claim 1 wherein the receiver includes a second transducer in line with or adjacent to a first transducer, wherein each transducer comprises an acoustic transducer configured for pulsed ultrasound velocimetry.

3. The system of claim 1 wherein said delay line element is arranged to optimise acoustic characteristics of said at least one transducer including one or more of: beam forming, focusing, coupling, impedance matching, beam path and sensor protection.

4. The system of claim 1 wherein the velocity estimating module is configured to apply simultaneously a time domain and/or a frequency domain algorithm to received backscattered ultrasonic signals from reflectors in the liquid flow, or data indicative thereof, in order to determine the instantaneous velocity profile of the liquid flow.

5. The system of claim 1 wherein the deconvolution module is configured to:
   receive the determined instantaneous velocity profile of the liquid flow from the velocity estimating module, a velocity of sound parameter, and a measured waveform shape corresponding to the received ultrasonic signal;
   determine a normalised sample window from the measured waveform shape by detecting an envelope of the measured waveform shape and dividing all sample points on the sample window by the sample window's maximum magnitude value;
   determine a length of the normalized sample window by multiplying a time axis associated with the measured waveform with the velocity of sound parameter;
   re-sample both recorded instantaneous velocity profile and determined sample window so that the number of samples correspond to correct distances of the sample window and radial distance of the stored instantaneous velocity profile;
   multiply the stored instantaneous velocity profile by an integral of the normalised sample window within the flow field to obtain a first multiplication product;
   apply a Fast Fourier Transform (FFT) algorithm to the first multiplication product to obtain a first FFT result;
   apply an FFT algorithm to the sample window/sample volume to obtain a second FFT result;
   divide the first FFT result by the second FFT result to obtain a first division quotient;
   apply a low pass filter to the first division quotient to obtain a low pass filtered first division quotient;
   apply an inverse FFT to the low pass filtered first division quotient to obtain the deconvolved velocity profile; and
   apply a smoothing filter to the deconvolved instantaneous profile in order to remove unwanted noise and enhance quality of the data.

6. The system of claim 1 wherein the fluid characterisation module is configured to:
   receive the determined instantaneous velocity profile of the liquid flow from the velocity estimating module, a velocity of sound parameter, and a measured waveform shape corresponding to the received ultrasonic signal;
   apply an appropriate smoothing filter to enhance the quality of the instantaneous velocity profile;
   apply a deconvolution procedure to the instantaneous velocity profile;
   apply a smoothing filter to the determined instantaneous velocity profiles and/or deconvolved instantaneous velocity profiles prior to obtaining a velocity gradient or shear rate distribution;
   apply numerical differentiation to the processed instantaneous velocity profile in order to calculate the maximum shear rate and shear rate distribution in the liquid flow.

7. The system of claim 1 wherein the system comprises a plurality of transducer configurations in order to obtain instantaneous three-dimensional velocity profiles.

8. The system of claim 5 wherein the deconvolution module is configured to continuously monitor the sample window.

9. The system of claim 1 wherein the at least one transducer is disposed at a non-orthogonal installation angle.

10. The system of claim 1 including one or more absolute or differential pressure sensors for obtaining a pressure difference between respective locations along a length of the pipe, and wherein the fluid characterisation module is configured to use the pressure difference from said pressure sensors and either the instantaneous velocity profile or the true instantaneous velocity profile to determine an instantaneous shear rate and shear stress distribution of the liquid flow.

11. The system of claim 10, wherein the fluid visualization and characterisation module is configured to determine instantaneous rheological properties of the liquid flow in the pipe by using the determined instantaneous shear rate and shear stress distribution.

12. The system of claim 10 which includes one or more temperature sensors.

13. A method for visualizing and characterising liquids flowing in a pipe defining a liquid flow path, the method comprising:
   converting an electric signal into an ultrasonic signal by using at least one transducer to transmit the ultrasonic signal into a liquid flowing in the pipe, the liquid having particle reflectors or bubble reflectors dispersed therewithin, and wherein when the ultrasonic signal is transmitted into the liquid flow in the pipe, reflectors in the liquid flow reflect the signal to form backscattered ultrasonic signals;
   receiving, by using a receiver, backscattered ultrasonic signals from reflectors in the liquid flow;
   applying, by using a processor, one or more velocity estimation algorithms to the received reflections of the ultrasonic signal, or data indicative thereof, to determine an instantaneous velocity profile of liquid flow in the pipe defining the liquid flow path, wherein the instantaneous velocity profile is a velocity distribution of liquid flow as a function of distance along a measuring axis of the pipe;
   applying, by using a processor, a deconvolution algorithm to the determined instantaneous velocity profile to determine a deconvolved instantaneous velocity profile of the liquid flow in the pipe defining the liquid flow path; and
   determining, by using a processor, instantaneous rheological properties of the liquid flow in the pipe by using the determined instantaneous velocity profiles and/or the deconvolved instantaneous velocity profiles;
   the method further comprising operating said at least one transducer with a delay line element arranged at a front of the transducer to optimise acoustic characteristics of said at least one transducer, and arranging said at least one transducer with the delay line element thereof in contact with an outer wall of said pipe defining a liquid flow path in a non-invasive measurement configuration, wherein the delay line element is configured so that a focal point of the ultrasonic signal transmitted by the transducer is located at a liquid-wall interface of the pipe where the ultrasonic signal enters the liquid flow path, when in use, thereby ensuring that no velocity measurements are made within a near-field distance of the transducer.

14. The method of claim 13, the method comprising receiving backscattered ultrasonic signals from reflections in the liquid flow by way of a second transducer associated with the first transducer.

15. The method of claim 14 wherein both a first transducer and a second transducer are operated in a transmit/receive mode, for measurement of instantaneous velocity profiles at opposed sides of the liquid flow path for symmetry, velocity of sound, acoustic characteristics, and flow rate using a transit time calculation method.

16. The method of claim 13 wherein applying the deconvolution algorithm comprises the steps of:
   receiving and storing the instantaneous velocity profile, a measured velocity of sound parameter, and a measured waveform shape;
   determining a normalised sample window from the measured waveform shape by detecting an envelope of the measured waveform shape and dividing all sample points on the sample window by the sample window's maximum magnitude value;
   determining a length of the normalized sample window by multiplying a time axis with the measured velocity of sound parameter;
   re-sampling both the stored instantaneous velocity profile and the determined sample window so that the number of samples correspond to correct distances of the sample window and radial distance of the stored instantaneous velocity profile;
   multiplying the stored instantaneous velocity profile by an integral of a sample window within the flow field to obtain a first multiplication product;
   applying a Fast Fourier Transform (FFT) algorithm to the first multiplication product to obtain a first FFT result;
   applying a FFT algorithm to the sample window to obtain a second FFT result;
   dividing the first FFT result by the second FFT result to obtain a first division quotient;
   applying a low pass filter in the frequency domain to the first division quotient to obtain a low pass filtered first division quotient;
   applying an inverse FFT to the low pass filtered first division quotient to obtain the deconvolved instantaneous velocity profile; and
   applying a smoothing filter to the deconvolved instantaneous profile in order to remove unwanted noise and enhance the quality of the data.

17. The method of claim 13 including applying, by using a processor, a non-model approach algorithm comprising the steps of:
   receiving the determined instantaneous velocity profile of the liquid flow from the velocity estimating module, a velocity of sound parameter, and a measured waveform shape corresponding to the received ultrasonic signal;
   applying an appropriate smoothing filter to enhance the quality of the instantaneous velocity profile;
   applying a deconvolution procedure to the instantaneous velocity profile;
   applying a smoothing filter to the determined instantaneous velocity profiles and/or deconvolved instantaneous velocity profiles prior to obtaining an instantaneous velocity gradient or shear rate distribution;
   applying numerical derivation to the processed instantaneous velocity profile; and
   calculating the maximum shear rate and shear rate distribution in the liquid flow.

18. The method of claim 13 including configuring a plurality of transducer pairs for transmitting and receiving a plurality of ultrasound signals and receiving associated backscattered ultrasonic signals from reflectors in the liquid flow in order to obtain instantaneous three-dimensional velocity profiles.

19. The method of claim 13 which includes:
   measuring a pressure difference over a fixed distance in the pipe defining the liquid flow path; and
   determining, by using a processor, an instantaneous shear rate and shear stress distribution of the liquid flow in the pipe by using the pressure difference from said pressure sensors and either the instantaneous velocity profile or the true instantaneous velocity profile.

20. The system of claim 19, which includes determining, by using a processor, instantaneous rheological properties of the liquid flow in the pipe by using the determined instantaneous shear rate and shear stress distribution of the liquid flow in the pipe.

21. A fluid visualization and characterisation system, including a signal processing system, the signal processing system including:
   a transmitter circuit for sending an electric signal to an ultrasonic transducer which is disposed exteriorly of a pipe having an outer wall, wherein the pipe defines a liquid flow path for flow of a liquid having particle or bubble reflectors dispersed therewithin, and wherein the transducer is configured to convert the electric signal into an ultrasonic signal and to transmit the ultrasonic signal into a liquid flow in the pipe and wherein the transducer is arranged to be used in conjunction with a delay line element which includes an acoustic wedge and acoustic couplant, and wherein the delay line element is provided at a front of the transducer and configured to enhance acoustic characteristics of the transducer, the delay line element being disposed in contact with an outer wall of said pipe in a non-invasive measurement configuration, and wherein, when the ultrasonic signal is transmitted into the liquid flow in the pipe, reflectors in the liquid flow reflect the signal to form backscattered ultrasonic signals;
   a receiver circuit for receiving signals from an ultrasonic transducer configured to receive the backscattered ultrasonic signals from reflectors in the liquid flow;
   a memory for storing data; and
   a processor operatively connected to the memory, the processor comprising:
      a velocity estimating module configured to apply one or more velocity estimation algorithms to received reflections of said ultrasonic signal, or data indicative thereof, to determine an instantaneous velocity profile of liquid flow in the liquid flow path, wherein the instantaneous velocity profile is a velocity distribution of liquid flow as a function of distance along a measuring axis of the pipe;
      a deconvolution module configured to apply a deconvolution algorithm at least to the determined instantaneous velocity profile to determine a true instantaneous velocity profile of the liquid flow in the liquid flow path; and
      a fluid visualization and characterisation module configured to determine instantaneous rheological properties of the liquid flow in the liquid flow path by using the determined instantaneous velocity profile and/or the true instantaneous velocity profile,
   wherein the delay line element is configured so that the focal point of the ultrasonic signal transmitted by the transducer is located at a liquid-wall interface of the pipe where the ultrasonic signal enters the liquid flow path, thereby ensuring that no velocity measurements are made within a near-field distance of the transducer.

22. The fluid visualization and characterisation system of claim 21 wherein the velocity estimating module is arranged to apply time domain and frequency domain velocity estimation algorithms simultaneously.

23. The system of claim 21 which includes one or more absolute or differential pressure sensors for obtaining a pressure difference between respective locations along a length of the pipe, and wherein the fluid characterisation module is configured to use the pressure difference from said pressure sensors and either the instantaneous velocity profile or the true instantaneous velocity profile to determine an instantaneous shear rate and shear stress distribution of the liquid flow.

24. The system of claim 23, wherein the fluid visualization and characterisation module is configured to determine instantaneous rheological properties of the liquid flow in the pipe by using the determined instantaneous shear rate and shear stress distribution.

* * * * *